(12) United States Patent
Bhat et al.

(10) Patent No.: US 12,371,624 B2
(45) Date of Patent: Jul. 29, 2025

(54) SYSTEMS AND PROCESSES FOR PRODUCING ETHYLENE FROM NAPHTHA AND BUTANES

(71) Applicant: Saudi Arabian Oil Company, Dhahran (SA)

(72) Inventors: Vishvedeep Bhat, Dhahran (SA); Vinod Ramaseshan, Dhahran (SA); Omer Refa Koseoglu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 18/416,472

(22) Filed: Jan. 18, 2024

(65) Prior Publication Data

US 2024/0166957 A1 May 23, 2024

Related U.S. Application Data

(63) Continuation of application No. 18/056,794, filed on Nov. 18, 2022, now Pat. No. 11,920,093.

(51) Int. Cl.
*C10G 35/09* (2006.01)
*B01D 3/14* (2006.01)
(Continued)

(52) U.S. Cl.
CPC ............. *C10G 35/09* (2013.01); *B01D 3/141* (2013.01); *C07C 4/04* (2013.01); *C07C 5/226* (2013.01)

(58) Field of Classification Search
CPC ........... B01D 3/141; C07C 4/04; C07C 5/226; C10G 35/09; C10G 45/60; C10G 69/06; C10G 9/36
See application file for complete search history.

(56) References Cited

U.S. PATENT DOCUMENTS 7,402,417 B2 7/2008 Croteau et al.
7,645,558 B2 1/2010 Norsten et al.
(Continued)

FOREIGN PATENT DOCUMENTS

EP 2243814 A1 10/2010

*Primary Examiner* — Ellen M McAvoy
*Assistant Examiner* — Chantel Graham
(74) *Attorney, Agent, or Firm* — DINSMORE & SHOHL LLP

(57) ABSTRACT

A process for upgrading a hydrocarbon feed includes contacting the hydrocarbon feed with hydrogen in the presence of a ring opening catalyst in a naphthene conversion unit, the contacting causing naphthenes in the hydrocarbon feed to react to produce a converted effluent comprising isoparaffins and normal paraffins. The process includes separating the converted effluent in a paraffin separation system to produce an isoparaffin-rich stream and an n-paraffin-rich stream. The process includes contacting the isoparaffin-rich stream with hydrogen in the presence of an isomerization catalyst in a reverse isomerization unit, the contacting causing isomerization to produce an isomerate comprising an equilibrium mixture of normal paraffins and isoparaffins. The process include separating the isomerate in the paraffin separation system to produce the isoparaffin-rich stream and the n-paraffin-rich stream, and passing the n-paraffin-rich stream to a steam cracker to produce a cracker effluent comprising olefins.

20 Claims, 5 Drawing Sheets

(51) Int. Cl.
*C07C 4/04* (2006.01)
*C07C 5/22* (2006.01)

(56) References Cited

U.S. PATENT DOCUMENTS

| | | |
|---|---|---|
| 10,260,011 B2 | 4/2019 | Ward et al. |
| 11,046,900 B2 | 6/2021 | Housmans et al. |
| 11,072,750 B2 | 7/2021 | Housmans et al. |
| 2005/0101814 A1 | 5/2005 | Foley et al. |
| 2008/0223754 A1* | 9/2008 | Subramanian ......... C10G 69/04 196/14.52 |
| 2016/0369188 A1* | 12/2016 | Housmans ............. C10G 65/10 |
| 2023/0078452 A1* | 3/2023 | Rokkam ................ C10G 45/58 585/738 |

\* cited by examiner

SYSTEMS AND PROCESSES FOR PRODUCING ETHYLENE FROM NAPHTHA AND BUTANES

CROSS-REFERENCE TO RELATED APPLICATION

The present application is a continuation of co-pending U.S. patent application Ser. No. 18/056,794, filed on Nov. 18, 2022 and entitled "Systems and Processes for Producing Ethylene from Naphtha and Butanes," the entire disclosure of which is incorporated by reference in the present disclosure.

BACKGROUND

Field

The present disclosure generally relates to processes and systems for upgrading hydrocarbons, more specifically, systems and processes for upgrading naphtha and butane streams to greater value chemical products and intermediates.

Technical Background

Hydrocarbon feeds, such as naphtha, can be converted to chemical products and intermediates such as olefins and aromatic compounds, which are basic intermediates for a large portion of the petrochemical industry. The worldwide increasing demand for light olefins and aromatic compounds remains a major challenge for many integrated refineries. In particular, the production of some valuable light olefins, such as ethylene, propene, and butenes, has attracted increased attention as pure olefin streams are considered the building blocks for polymer synthesis. Further the processing of naphtha streams, such as hydrocracked naphtha, straight run naphtha, or both, may be desirable, as light naphtha possesses a low octane number and its use in fuel production is limited.

SUMMARY

In addition to ethane and propane, straight run naphtha and straight run butanes are the most common feedstocks for steam cracking processes to produce primarily ethylene. Many refiners and petrochemical companies are also looking at max naphtha hydrocrackers or slurry phase hydrocrackers to maximize naphtha production to provide greater quantities of naphtha feedstocks for stream cracking to produce ethylene. However, the straight run naphtha and hydrocracked naphtha streams can have high naphthene content (40 wt. % to 60 wt. %) and high molar ratios of isoparaffins to normal paraffins (2-4), both of which reduce the ethylene yields from steam cracking the straight run naphthas or hydrocracked naphthas. This can increase the overall cost of production of ethylene from the steam cracking process. Further, butanes produced from hydrocracking and reforming units are also rich in isobutane, isobutene, or both, which tend to produce three times less ethylene than compared to normal butanes when subjected to steam cracking.

Accordingly, there is an ongoing need for systems and methods of increasing the yield of ethylene from steam cracking naphtha streams, butane-containing streams, or both. The systems and processes of the present disclosure are directed to processing naphtha streams in a naphtha conversion unit to convert naphthenes to paraffins and then isomerizing isoparaffin compounds to normal paraffin compounds in a reverse isomerization system. Butane-containing streams can be introduced to the reverse isomerization system to convert isobutanes to normal butane. Converting naphthenes to paraffins and isomerizing isoparaffins to normal paraffins can increase the yield of ethylene from a steam cracking process and can reduce the cost of operating the steam cracking process, among other features.

According to one or more aspects of the present disclosure, a process for upgrading a hydrocarbon feed may comprise passing the hydrocarbon feed to a naphthene conversion unit, where the hydrocarbon feed may comprise naphthenes. The process may further comprise contacting the hydrocarbon feed with hydrogen in the presence of a ring opening catalyst in the naphthene conversion unit, where the contacting may cause at least a portion of the naphthenes in the hydrocarbon feed to react to produce a converted effluent comprising at least isoparaffins and normal paraffins. The process may further include passing at least a portion of the converted effluent to a paraffin separation system that may separate the at least a portion of the converted effluent to produce least one isoparaffin-rich stream and at least one n-paraffin-rich stream. The process may further include passing the at least one isoparaffin-rich stream to a reverse isomerization unit and contacting the at least one isoparaffin-rich stream with hydrogen in the presence of an isomerization catalyst in the reverse isomerization unit, where the contacting in the reverse isomerization unit may cause at least a portion of the isoparaffins in the at least one isoparaffin-rich stream to undergo isomerization to produce an isomerate comprising a mixture of normal paraffins and isoparaffins. The process may further include passing at least a portion of the isomerate to the paraffin separation system that may separate the at least a portion of the isomerate to produce the at least one isoparaffin-rich stream and the at least one n-paraffin-rich stream, and passing the at least one n-paraffin-rich stream to a steam cracker to produce a cracker effluent comprising at least one product.

In another aspect of the present disclosure, a system for upgrading a hydrocarbon feed may comprise a naphthene conversion unit comprising a ring opening catalyst, the naphthene conversion unit operable to convert naphthenes from a naphtha feed to produce a converted effluent comprising a mixture of isoparaffins and n-paraffins; a reverse isomerization unit disposed downstream of the naphthene conversion unit, the reverse isomerization unit comprising an isomerization catalyst and operable to convert isoparaffins from at least one isoparaffin rich stream to n-paraffins to produce an isomerate comprising a concentration of n-paraffins greater than a concentration of n-paraffins in the at least one isoparaffin-rich stream; a paraffin separation system operable to separate at least a portion of the converted effluent and at least a portion of the isomerate to produce the at least one isoparaffin-rich stream and at least one n-paraffin-rich stream; and a steam cracker disposed downstream of the paraffin separation system and operable to steam crack the at least one n-paraffin-rich stream to produce a cracker effluent comprising at least ethylene.

Additional features and advantages of the technology described in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
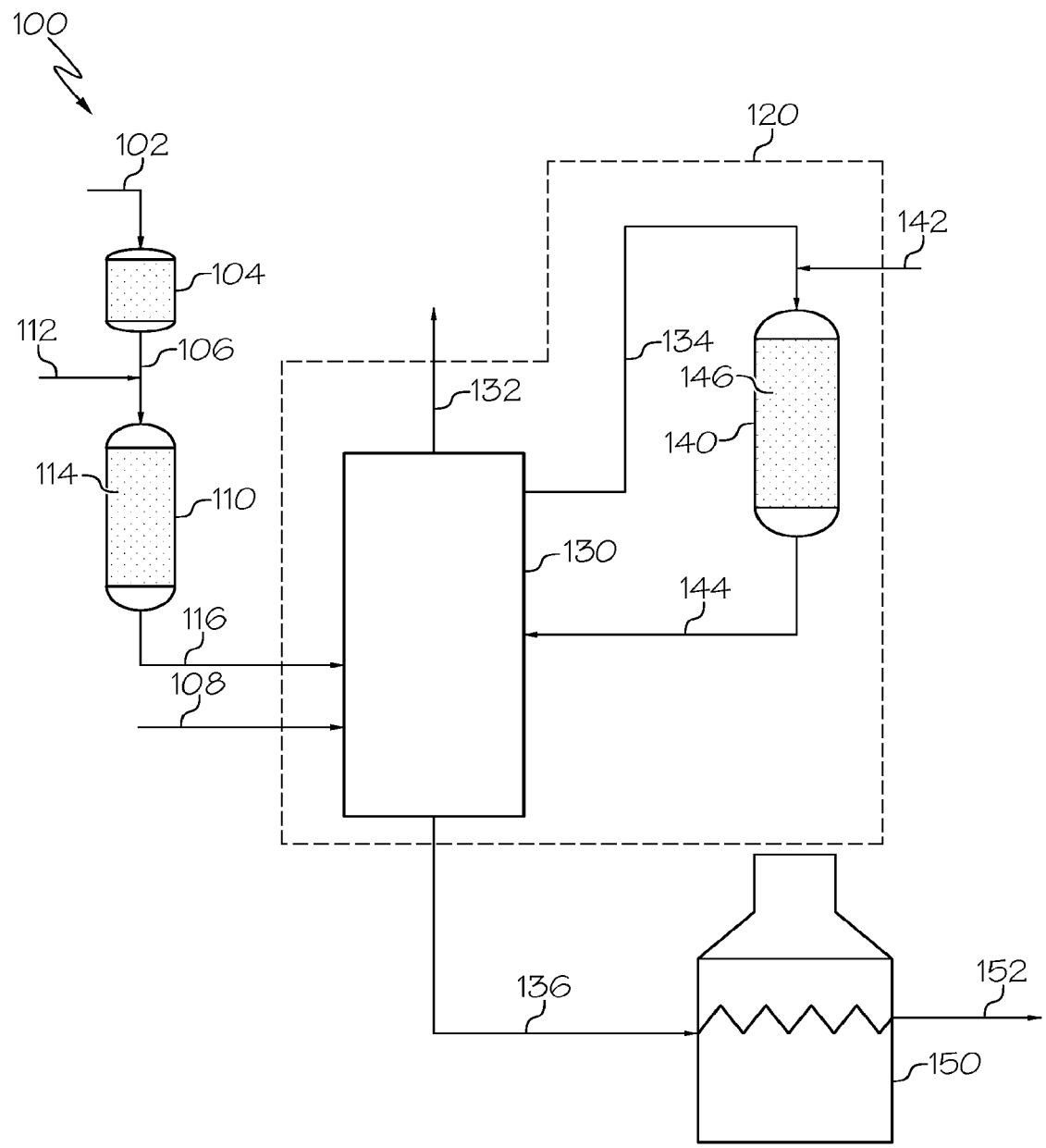
FIG. 1 schematically depicts a generalized flow diagram of a system for upgrading a naphtha feed, according to one or more embodiments shown and described in this disclosure.

For the purpose of describing the simplified schematic illustrations and descriptions of FIGS. 1-5, the numerous valves, temperature sensors, electronic controllers, and the like that may be employed and well known to those of ordinary skill in the art of certain chemical processing operations are not included. Further, accompanying components that are often included in chemical processing operations, such as, for example, air supplies, heat exchangers, surge tanks, catalyst hoppers, pumps, valves, flow controllers, instruments, or other related systems are not depicted. It would be known that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines that may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows that do not connect two or more system components signify a product stream which exits the depicted system or a system inlet stream which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a system product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that two or more process streams are "mixed" or "combined" when two or more lines intersect in the schematic flow diagrams of FIGS. 1-5. Mixing or combining may also include mixing by directly introducing both streams into a like reactor, separation device, or other system component. For example, it should be understood that when two streams are depicted as being combined directly prior to entering a separation unit or reactor, that in some embodiments the streams could equivalently be introduced into the separation unit or reactor and be mixed in the reactor.

Reference will now be made in greater detail to various embodiments of the present disclosure, some embodiments of which are illustrated in the accompanying drawings. Whenever possible, the same reference numerals will be used throughout the drawings to refer to the same or similar parts.

DETAILED DESCRIPTION

The present disclosure is directed to systems and processes for upgrading a naphtha feed, a butane-containing stream, or both upstream of a steam cracking process to increase the yield of ethylene from the steam cracking process. Referring to FIG. 1, one embodiment of the systems 100 of the present disclosure for upgrading the hydrocarbon feed can include a naphthene conversion unit 110 comprising a ring opening catalyst 114, where the naphthene conversion unit is operable to convert naphthenes from a naphtha feed 102 to produce a converted effluent 116 comprising a mixture of isoparaffins and n-paraffins. The systems 100 may include a reverse isomerization unit 140 disposed downstream of the naphthene conversion unit 110, where the reverse isomerization unit 140 may comprise an isomerization catalyst 146 and may be operable to convert isoparaffins from at least one isoparaffin-rich stream 134 to n-paraffins to produce an isomerate 144 comprising a concentration of n-paraffins greater than a concentration of n-paraffins in the at least one isoparaffin-rich stream 134. The systems 100 may further include a paraffin separation system 130 operable to separate at least a portion of the converted effluent 116 and at least a portion of the isomerate 144 to produce the at least one isoparaffin-rich stream 134 and at least one n-paraffin-rich stream 136 and a steam cracker disposed downstream of the paraffin separation system 130 and operable to steam crack the at least one n-paraffin-rich stream 136 to produce a cracker effluent 152 comprising at least one product. In embodiments, the product may be ethylene.

The systems 100 may be used in processes for upgrading the hydrocarbon feed. The processes may include passing the hydrocarbon feed, such as but not limited to the naphtha feed 102, to the naphthene conversion unit 110, where the hydrocarbon feed comprises at least naphthenes. The processes may further include contacting the hydrocarbon feed with hydrogen 112 in the presence of the ring opening catalyst 114 in the naphthene conversion unit 110, where the contacting may cause at least a portion of the naphthenes in the hydrocarbon feed to react to produce the converted effluent 116 comprising at least isoparaffins and normal paraffins. The processes may further include separating at least a portion of the converted effluent 116 in a paraffin separation system 130 to produce at least one isoparaffin-rich stream 134 and at least one n-paraffin-rich stream 136, passing the at least one isoparaffin-rich stream 134 to the reverse isomerization unit 140, and contacting the at least one isoparaffin-rich stream 134 with hydrogen 142 in the presence of the isomerization catalyst 146 in the reverse isomerization unit 140, where the contacting in the reverse isomerization unit 140 may cause at least a portion of the isoparaffins in the at least one isoparaffin-rich stream 134 to undergo isomerization to produce the isomerate 144 comprising a mixture of normal paraffins and isoparaffins. In embodiments, a concentration of normal paraffins in the isomerate is greater than the concentration of normal paraffins in the isoparaffin-rich stream 134 passed to the reverse isomerization unit 140. The processes may further include passing at least a portion of the isomerate 144 to the paraffin separation system 130 that separates the portion of the isomerate 144 to produce the at least one isoparaffin-rich stream 134 and the at least one n-paraffin-rich stream 136 and passing the at least one n-paraffin-rich stream 136 to the steam cracker 150 to produce the cracker effluent 152, which may comprise at least one product. The systems 100 and processes of the present disclosure may increase ethylene yield compared to steam cracking compared to steam cracking naphtha feeds and butane containing streams directly.

As used in this disclosure, a "catalyst" refers to any substance that increases the rate of a specific chemical reaction. Catalysts and catalyst components described in this disclosure may be utilized to promote various reactions, such as, but not limited to cracking, aromatic cracking, or combinations of these.

As used in this disclosure, "cracking" refers to a chemical reaction where a molecule having carbon-carbon bonds is broken into more than one molecule by the breaking of one or more of the carbon-carbon bonds; where a compound including a cyclic moiety, such as an aromatic, is converted to a compound that does not include a cyclic moiety; or where a molecule having carbon-carbon double bonds are reduced to carbon-carbon single bonds. Some catalysts may have multiple forms of catalytic activity, and calling a catalyst by one particular function does not render that catalyst incapable of being catalytically active for other functionality.

As used throughout the present disclosure, the term "light olefins" refers to one or more of ethylene, propylene, butenes, or combinations of these.

As used throughout the present disclosure, the term "butane" or "butanes" refers to normal butane (n-butane), isobutane, or a combination of n-butane and isobutane.

As used throughout the present disclosure, the term "crude oil" or "whole crude oil" refers to crude oil received directly from an oil field or from a desalting unit without having any fraction separated by distillation.

As used throughout the present disclosure, the term "naphtha" generally refers to hydrocarbons having from 5 to 12 carbon atoms, hydrocarbons having boiling point temperatures in a range of from 36° C. to 220° C., or both.

As used throughout the present disclosure, the term "dry gas" refers to hydrocarbons having 1 or 2 carbon atoms, which includes methane and C2 hydrocarbons such as ethane, ethylene, and acetylene.

As used throughout the present disclosure, the terms "upstream" and "downstream" may refer to the relative positioning of unit operations with respect to the direction of flow of the process streams. A first unit operation of a system may be considered "upstream" of a second unit operation if process streams flowing through the system encounter the first unit operation before encountering the second unit operation. Likewise, a second unit operation may be considered "downstream" of the first unit operation if the process streams flowing through the system encounter the first unit operation before encountering the second unit operation.

As used in the present disclosure, passing a stream or effluent from one unit "directly" to another unit may refer to passing the stream or effluent from the first unit to the second unit without passing the stream or effluent through an intervening reaction system or separation system that substantially changes the composition of the stream or effluent. Heat transfer devices, such as heat exchangers, preheaters, coolers, condensers, or other heat transfer equipment, and pressure devices, such as pumps, pressure regulators, compressors, or other pressure devices, are not considered to be intervening systems that change the composition of a stream or effluent. Combining two streams or effluents together also is not considered to comprise an intervening system that changes the composition of one or both of the streams or effluents being combined. Simply dividing a stream into two streams having the same composition is also not considered to comprise an intervening system that changes the composition of the stream.

As used in this disclosure, a "separation unit" refers to any separation device that at least partially separates one or more chemicals that are mixed in a process stream from one another. For example, a separation unit may selectively separate differing chemical species from one another, forming one or more chemical fractions. Examples of separation units include, without limitation, distillation columns, divided wall columns, flash drums, knock-out drums, knock-out pots, centrifuges, filtration devices, traps, scrubbers, expansion devices, adsorption devices, membranes, solvent extraction devices, and the like. It should be understood that separation processes described in this disclosure may not completely separate all of one chemical consistent from all of another chemical constituent. It should be understood that the separation processes described in this disclosure "at least partially" separate different chemical components from one another, and that even if not explicitly stated, it should be understood that separation may include only partial separation. As used in this disclosure, one or more chemical constituents may be "separated" from a process stream to form a new process stream. Generally, a process stream may enter a separation unit and be divided or separated into two or more process streams of desired composition. Further, in some separation processes, a "light fraction" and a "heavy fraction" may separately exit the separation unit. In general, the light fraction stream has a lesser boiling point than the heavy fraction stream. It should be additionally understood that where only one separation unit is depicted in a figure or described, two or more separation units may be employed to carry out the identical or substantially identical separation. For example, where a distillation column with multiple outlets is described, it is contemplated that several separators arranged in series may equally separate the feed stream and such embodiments are within the scope of the presently described embodiments.

As used in this disclosure, the term "effluent" may refer to a stream that is passed out of a reactor, a reaction zone, or a separation unit following a particular reaction or separation. Generally, an effluent has a different composition than the stream that entered the separation unit, reactor, or reaction zone. It should be understood that when an effluent is passed to another system unit, only a portion of that system stream may be passed. For example, a slip stream (having the same composition) may carry some of the effluent away, meaning that only a portion of the effluent may enter the downstream system unit. The term "reaction effluent" may more particularly be used to refer to a stream that is passed out of a reactor or reaction zone.

It should further be understood that streams may be named for the components of the stream, and the component for which the stream is named may be the major component of the stream (such as comprising from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. For example, a disclosed "naphtha stream" passing to a first system component or from a first system component to a second system component should be understood to equivalently disclose "naphtha" passing to the first system component or passing from a first system component to a second system component.

The naphtha streams and butane-containing streams are primarily obtained from hydrocarbon refineries, where these streams are produced directly through the crude oil distillation process units (known as straight run naphtha and straight run butanes) and through secondary process units like fluidized catalytic cracking units, hydrocracking processes, coker units, or other refinery processes. "Straight run naphtha" refers to a naphtha stream produced through distillation of crude oil. "Straight run butanes" or "straight run C4 streams" refer to C4 streams produced primarily through distillation of crude oil. The term "hydrocracked naphtha" refers to a naphtha stream produced through hydrocracking of one or more hydrocarbon feeds.

Straight run naphtha streams have been conventionally used as the primary liquid feed stock for steam crackers. However, as refiners strive to increase the production of petrochemical products and intermediates, such as light olefins, from crude oil, hydrocracker naphtha is gaining in significance as a feedstock for steam cracking. Max naphtha hydrocrackers have been part of various crude to chemical configurations as the source of feedstock for the steam crackers along-side the straight run naphtha. The key issues with using hydrocracked naphtha as a feedstock to steam cracking processes are the high naphthene content (40 wt. % to 60 wt % typically) and the high concentration of isoparaffin compounds (mole ratio of isoparaffins to normal paraffins of 2:1-4:1), both of which can lead to 20-40% less ethylene production and increased production of low value byproducts from the steam cracking process.

While straight run naphtha generally has lower concentrations of naphthenes and isoparaffins compared to hydrocracked naphthas, there are still opportunities to reduce the naphthene content and the isoparaffinic content in straight run naphtha streams to increase the ethylene yield from steam cracking the straight run naphtha streams. Further, straight run naphtha streams can include aromatic compounds, which can also reduce ethylene yield from steam cracking. Typical dearomatization units operate to remove the aromatic compounds from the straight run naphtha streams through one or more separation steps. However, removing the aromatic compounds from straight run naphtha increases the process cost and reduces the overall yield of ethylene from the original straight run naphtha stream by removing hydrocarbons from the straight run naphtha.

Further, butanes produced from hydrocracking and reforming units are also rich in isobutane, isobutene, or both, which tend to produce three times less ethylene than compared to normal butanes when subjecting the butane-containing stream to steam cracking.

The present disclosure is directed to systems and processes for upgrading naphtha streams, butane-containing streams, or both upstream of a steam cracker to increase the yield of ethylene from steam cracking the naphtha streams, butane-containing streams, or both. The systems and processes of the present disclosure include a naphthene conversion unit and a reverse isomerization system, where the naphthene conversion unit converts naphthenes from the naphtha feed to paraffin compounds, and the reverse isomerization system isomerizes isoparaffins from the effluent from the naphthene conversion unit, a butane-containing stream, or both to normal paraffins.

Figure 2:
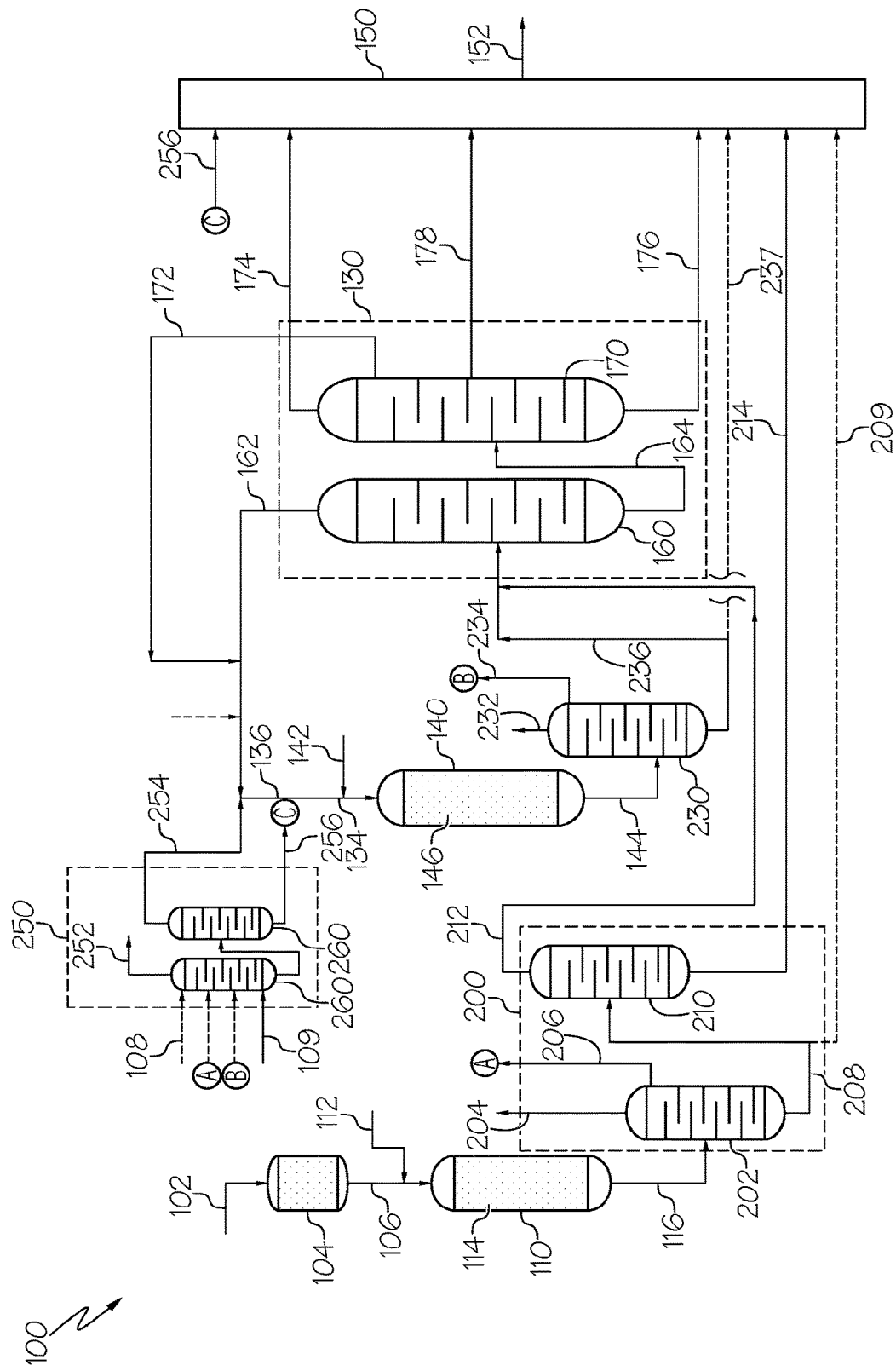
FIG. 2 schematically depicts a generalized flow diagram of another system for upgrading a naphtha feed, including desulfurizing the naphtha feed, according to one or more embodiments shown and described in this disclosure.

Referring now to FIG. 1, the systems 100 of the present disclosure may include a naphthene conversion unit 110 and a reverse isomerization system 120 disposed downstream of the naphthene conversion unit 110. The naphthene conversion unit 110 may be operable to convert naphthenes in a naphtha feed 102 to paraffins to produce a converted effluent 116. The naphthene conversion unit 110 may also partially convert at least a portion of the aromatic compounds in the naphtha feed 102. Referring to FIG. 2, in embodiments, the converted effluent 116 may be separated into a light naphtha 212 and a heavy naphtha 214. The heavy naphtha may 214 may be passed directly to the steam cracker. The light naphtha 212 along with a butane-containing stream 108 can be passed to reverse isomerization system 120.

Referring again to FIG. 1, the reverse isomerization system 120 may include a paraffin separation system 130 and a reverse isomerization unit 140 disposed downstream of the paraffin separation unit 140. The reverse isomerization system 120 may separate isoparaffins and normal paraffins from the converted effluent 116, the butane-containing stream 108, or both, to produce at least one isoparaffin-rich stream 134 and at least one n-paraffin-rich stream 136 and may isomerize isoparaffins from the isoparaffin-rich stream 134 to normal paraffins in the reverse isomerization unit 140. The n-paraffin-rich stream 136 may be passed to the steam cracker 150. The naphthene conversion unit 110 and reverse isomerization system 120 are integrated with a steam cracker 150 to increase the yield of ethylene from the steam cracker 150 compared to steam cracking a naphtha feed, with or without a butane-containing stream, without naphthene conversion and isomerization.

The systems 100 and processes of the present disclosure may increase the yield of ethylene from steam cracking a naphtha feed, a butane-containing feed, or both by converting naphthenes to paraffins and isomerizing isoparaffins to normal paraffins upstream of the steam cracker. The systems 100 and processes of the present disclosure may also enable greater process flexibility by being able to modify the ratio of ethylene to propylene produced in the steam cracker. Further, the systems 100 and processes of the present disclosure may also provide for hydrogenating aromatic compounds from the naphtha feed to further increase ethylene yield, among other features.

Referring again to FIG. 1, the systems 100 may include the naphthene conversion unit 110, the reverse isomerization system 120 disposed downstream of the naphthene conversion unit 110, and the steam cracker 150 downstream of the naphthene conversion unit 110 and the reverse isomerization system 130. The reverse isomerization unit 120 may comprise the paraffin separation system 130 and the reverse isomerization unit 140. In embodiments, the system 100 may further include a guard bed 104 disposed upstream of the naphthene conversion unit 110.

Referring again to FIG. 1, a naphtha stream 102 may be introduced to the system 100. Additionally, a butane-containing stream 108 can also be introduced to the system 100. The naphtha feed 102 may be a full range naphtha having a boiling point temperature range of from 36° C. to 220° C. In embodiments, the naphtha feed 102 may include hydrocarbons having a number of carbons of from 5 to 12. In other words, the naphtha feed 102 may have a carbon number of from 5 to 12. In embodiments, the naphtha feed 102 may have a molar ratio of isoparaffins to normal paraffins of greater than 1:2, greater than or equal to 1:1, or even greater than or equal to 2:1. In embodiments, the naphtha feed 102 may have a molar ratio of isoparaffins to normal paraffins of from 1:2 to 4:1, from 1:2 to 3:1, from 1:1 to 4:1, from 1:1 to 3:1, from 2:1 to 4:1, or from 2:1 to 3:1. In embodiments, the naphtha feed 102 may comprise a hydrocracked naphtha and may have a molar ratio of isoparaffins to normal paraffins of from 2:1 to 4:1. In embodiments, the naphtha feed 102 may comprise a straight run naphtha and may have a molar ratio of isoparaffins to normal paraffins of from 1:2 to 4:1. In embodiments, the naphtha feed 102 may have a concentration of water that is less than the saturation limits for the naphthene conversion unit 110.

The naphtha feed 102 may comprise a straight run naphtha, a hydrocracked naphtha, or both. In embodiments, the naphtha feed 102 may comprise a hydrocracked naphtha. Hydrocracking is a high hydrogen partial pressure process that converts heavy molecules boiling at temperatures greater than 350° C. lighter components, such as hydrocracked naphtha and diesel boiling range hydrocarbons. Since the catalysts used for hydrocracking are acidic, the hydrocracking process produces a naphtha fraction with high concentration of isoparaffins to normal paraffins, such as from 2:1 to 4:1. Aromatic saturation reactions also take place in the hydrocracking unit so hydrocracked naphtha also contains naphthenes. Therefore, when the naphtha feed 102 comprises a hydrocracked naphtha, the naphtha feed 102 can have high concentrations of isoparaffins and naphthenes.

In embodiments, the naphtha feed 102 may include a straight run naphtha. As previously discussed, straight run naphthas may have lower concentrations of naphthenes and isoparaffins compared to hydrocracked naphthas. However, the straight run naphthas can still have significant concentrations of naphthenes and isoparaffins. Further, straight run naphtha streams can include aromatic compounds. Thus, when the naphtha feed 102 comprises a straight run naphtha, the naphtha feed 102 may have a significant concentration of naphthenes and isoparaffins. Straight run naphtha may also include sulfur, metals, and other contaminants that may need to be removed upstream of the naphthene conversion unit 110.

In embodiments, a butane-containing stream 108 may be introduced to the system 100. The butane-containing stream 108 may be a C4 stream from any hydrocarbon refinery process or combinations of refinery processes. In embodiments, the butane-containing stream 108 may be a straight run C4 stream obtained from distillation of crude oil. In embodiments, the butane-containing stream 108 may include butane-containing streams from refinery systems, such as but not limited to C4 streams from fluidized catalytic cracking systems, hydrocracking systems, steam crackers, hydrotreating units, residue conversion units, visbreaking, delayed cokers, residue hydroprocessing, other refinery processes, or combinations of these. The butane-containing stream 108 may have a concentration of isobutane high enough to reduce the yield of ethylene from steam cracking the butane-containing stream by a factor of 2 compared to a steam cracking normal butane by itself. As previously discussed, each mole of isobutane produces 3 times less ethylene during steam cracking compared to a mole of normal butane. In embodiments, the butane-containing stream 108 may comprise greater than or equal to 5 wt. % isobutane, greater than or equal to 10 wt. % isobutane, greater than or equal to 20 wt. % isobutane, or greater than or equal to 30 wt. % isobutane, based on the total weight of the butane-containing stream. In embodiments, the butane-containing stream 108 may comprise from 5 wt. % to 90 wt. % isobutane, such as from 5 wt. % to 75 wt. %, from 5 wt. % to 50 wt. %, from 10 wt. % to 90 wt. %, from 10 wt. % to 75 wt. %, from 10 wt. % to 50 wt. %, from 20 wt. % to 90 wt. %, from 20 wt. % to 75 wt. %, from 20 wt. % to 50 wt. %, from 30 wt. % to 90 wt. %, from 30 wt. % to 75 wt. %, from 30 wt. % to 50 wt. %, or from 50 wt. % to 90 wt. % isobutane based on the total weight of the butane-containing stream 108.

The butane-containing stream 108 can be combined with the naphtha feed 102 upstream of the naphthene conversion unit 110 or can be introduced separately to the reverse isomerization system 120. In embodiments, the feed to the naphthene conversion unit 110 may include both the naphtha feed 102 and the butane-containing stream 108. In these embodiments, the feed to the naphthene conversion unit 110 may have a carbon number of from 4 to 12, a boiling point temperature range of from −5° C. to 220° C., or both. Since the butane-containing stream 108 generally does not include aromatic compounds or naphthenes, in embodiments, the butane-containing stream 108 may be passed to the reverse isomerization system 120, such as to the paraffin separation system 130 of the reverse isomerization system 120, as shown in FIG. 1.

Referring now to FIG. 2, in embodiments, one or more liquid petroleum gas (LPG) streams 109 or other C4 streams may be introduced to the system, such as to the paraffin separation system 130 of the reverse isomerization system 120. The other C4 streams may be butane-containing effluents from refinery systems other than distillation of crude oil, such as from fluidized catalytic cracking systems, hydrocracking systems, steam crackers, hydrotreating units, residue conversion units, visbreaking, delayed cokers, residue hydroprocessing, other refinery processes, or combinations of these.

Referring again to FIG. 1, in embodiments, the naphtha feed 102 may be passed to the guard bed 104 upstream of the naphthene conversion unit 110. The guard bed 104 may be operable to remove heteroatom-containing compounds and metals from the naphtha feed 102 to produce a conditioned naphtha feed 106. Heteroatom-containing compounds, such as but not limited to sulfur-containing compounds, nitrogen-containing compounds, or combinations of these, may reduce the catalytic activity of the catalyst in the naphthene conversion unit 110. As previously discussed, heteroatoms and metals may be present in naphtha feeds 102 that include straight run naphthas, in particular. Therefore, these heteroatom-containing compounds and metals are removed by the guard bed 104 upstream of the naphthene conversion unit 110 to retain the catalytic activity and improve the service life of the catalyst in the naphthene conversion unit 110.

The guard bed 104 may contain one or a plurality of catalysts operable to remove sulfur compounds, metals, or both from the naphtha feed 102. In embodiments, the guard bed 104 may comprise a desulfurization catalyst, a denitrogenation catalyst, or both. The conditioned naphtha feed 106 may have a concentration of sulfur of less than or equal to 0.5 parts per million by weight based on the weight of the conditioned naphtha feed 106.

Referring again to FIG. 1, the conditioned naphtha feed 106 may be passed from the guard bed 104 directly to the naphthene conversion unit 110. In embodiments, the naphtha feed 102 may be passed directly to the naphthene conversion unit 110 without passing through the guard bed 104. Hydrogen 112 may be passed to the naphthene conversion unit 110. The hydrogen 112 may be passed directly to the naphthene conversion unit 110 or combined with the conditioned naphtha feed 106 upstream of the naphthene conversion unit 110. The hydrogen 112 can be supplied directly from the hydrogen header, such as from the make-up hydrogen gas compressor. In embodiments, the hydrogen 112 may be recovered hydrogen from a hydrocracker unit, such as from an amine scrubbed off gas from a flash drum of any hydrocracker unit.

The naphthene conversion unit 110 may be operable to contact the naphtha feed 102 or the conditioned naphtha feed 106 with the hydrogen 112 in the presence of a ring opening catalyst 114 at reaction conditions designed to convert the naphthenes from the naphtha feed 102 or conditioned naphtha feed 106 to paraffins. Contacting the naphtha feed 102 or the conditioned naphtha feed 106 with the hydrogen 112 in the presence of a ring opening catalyst 114 at reaction conditions may also at least partially convert aromatic compounds to saturated compounds, such as by hydrogenating the aromatic rings to produce additional naphthenes or hydrogenating and cracking the aromatics to produce additional paraffins. Contacting the naphtha feed 102 or the conditioned naphtha feed 106 with the hydrogen 112 in the presence of a ring opening catalyst 114 at the reaction conditions may also minimize dry gas yield.

The naphthene conversion unit 110 may include one or a plurality of naphthene conversion reactors. In embodiments, the naphthene conversion unit 110 may include multiple naphthene conversion reactors arranged in series. The naphthene conversion reactors may be fixed-bed reactors, ebullated bed reactors, moving bed reactors, or combinations of these. In embodiments, the naphthene conversion unit 110 may comprise at least one naphthene conversion reactor that is a fixed bed reactor. In embodiments, the naphthene conversion reactor of the naphthene conversion unit 110 may be a three phase reactor in which the hydrogen 112 is present in a gas phase, the naphtha feed 102 or conditioned naphtha feed 106 is in a liquid phase, and the ring opening catalyst is in a solid phase. In embodiments, the naphthene conversion reactor of the naphthene conversion unit 110 may be a two-phase reactor where the hydrogen 112 is dissolved into the liquid phase comprising the naphtha feed 102 or conditioned naphtha feed 106, and the ring opening catalyst is in a solid phase.

The ring opening catalyst 114 may comprise one or more catalytic metals supported on a catalyst support. The catalytic metals may be any metals in groups 8-10 of the International Union of Pure and Applied Chemistry (IUPAC) periodic table of elements. In embodiments, the catalytic metal may comprise one or more metals selected from the group consisting of iridium (Ir), platinum (Pt), palladium (Pd), rhodium (Rh), ruthenium (Ru), and combinations of these. In embodiments, the metals can be present as the pure metal compounds. The catalyst support may include amorphous or crystalline oxides of alumina, silica, titania, or combinations of these. The catalyst support may be non-acidic or only mildly acidic. If the acidity of the catalyst support is too high, then the ring opening catalyst may have reduced activity for converting naphthenes to paraffins.

The naphthene conversion reactors of the naphthene conversion unit 110 may be operated at conditions that promote conversion of naphthenes to paraffins and that may result in at least partially converting any aromatic compounds from the naphtha feed 102 to saturated linear, branched, or cyclic hydrocarbons. The naphthene conversion reactors of the naphthene conversion unit 110 may be operated at an operating temperature of from 150° C. to 400° C., such as from 150° C. to 375° C., from 150° C. to 350° C., from 150° C. to 325° C., from 150° C. to 300° C., from 150° C. to 275° C., from 175° C. to 400° C., from 175° C. to 375° C., from 175° C. to 350° C., from 175° C. to 325° C., from 175° C. to 300° C., from 175° C. to 275° C., from 200° C. to 400° C., from 200° C. to 375° C., from 200° C. to 350° C., from 200° C. to 325° C., from 200° C. to 300° C., from 200° C. to 275° C., from 250° C. to 400° C., from 250° C. to 375° C., from 250° C. to 350° C., from 250° C. to 325° C., from 250° C. to 300° C., from 250° C. to 275° C., from 275 to 400° C., from 275° C. to 375° C., from 275° C. to 350° C., from 300° C. to 400° C., from 300° C. to 375° C., from 300° C. to 350° C., from 325° C. to 400° C., from 325° C. to 375° C., or from 350° C. to 400° C.

The naphthene conversion reactors of the naphthene conversion unit 110 may be operated at an operating pressure of from 1,000 kilopascals (kPa) (10 bar) to 10,000 kPa (100 bar), such as from 1,000 kPa to 9,000 kPa, from 1,000 kPa to 8,000 kPa, from 1,000 kPa to 7,000 kPa, from 1,000 kPa to 6,000 kPa, from 2,000 kPa to 10,000 kPa, from 2,000 kPa to 9,000 kPa, from 2,000 kPa to 8,000 kPa, from 2,000 kPa to 7,000 kPa, or from 2,000 kPa to 6,000 kPa. The naphthene conversion reactors of the naphthene conversion unit 110 may be operated at a hydrogen partial pressure of from 1,000 kPa to 6,000 kPa, such as from 1,000 kPa to 5,000 kPa, from 1,000 kPa to 4,000 kPa, from 1,000 kPa to 3,000 kPa, from 1,000 kPa to 2,000 kPa, from 2,000 kPa to 6,000 kPa, from 2,000 kPa to 5,000 kPa, from 2,000 kPa to 4,000 kPa, from 2,000 kPa to 3,000 kPa, or from 3,000 kPa to 6,000 kPa. The naphthene conversion reactors of the naphthene conversion unit 110 may be operated at a liquid hourly space velocity (LHSV) of from 0.2 per hour ($h^{-1}$) to 20 $h^{-1}$, such as from 0.2 $h^{-1}$ to 10 $h^{-1}$, from 0.2 $h^{-1}$ to 5 $h^{-1}$, from 0.2 $h^{-1}$ to 3 $h^{-1}$, from 0.2 $h^{-1}$ to 2 $h^{-1}$, from 0.5 $h^{-1}$ to 20 $h^{-1}$, from 0.5 $h^{-1}$ to 10 $h^{-1}$, from 0.5 $h^{-1}$ to 5 $h^{-1}$, from 0.5 $h^{-1}$ to 3 $h^{-1}$, from 0.5 $h^{-1}$ to 2 $h^{-1}$, from 1 $h^{-1}$ to 20 $h^{-1}$, from 1 $h^{-1}$ to 10 $h^{-1}$, from 1 $h^{-1}$ to 5 $h^{-1}$, from 1 $h^{-1}$ to 3 $h^{-1}$, from 1 $h^{-1}$ to 2 $h^{-1}$, from 2 $h^{-1}$ to 20 $h^{-1}$, from 2 $h^{-1}$ to 10 $h^{-1}$, or from 2 $h^{-1}$ to 2 $h^{-1}$.

A converted effluent 116 may be passed out of the naphthene conversion unit 110. The conversion of naphthenes to paraffins in the naphthene conversion unit 110 may be greater than or equal to 95 wt %, greater than or equal to 96 wt. %, greater than or equal to 97 wt. % greater than or equal to 98 wt. %, or even greater than or equal to 99 wt. % based on the total concentration of the naphthenes from the naphtha feed 102. Conversion of aromatic compounds to saturated linear, branched, or cyclic hydrocarbon compounds may also proceed to a great extend in the naphthene conversion unit 110. The naphthene conversion unit 110 may also minimizing the dry gas yield and minimize the ratio of isoparaffins to normal paraffins in the converted effluent 116.

The converted effluent 116 may have a concentration of paraffins greater than a concentration of paraffins in the naphtha feed 102, the conditioned naphtha feed 106, or both. In embodiments, the converted effluent 116 may have a concentration of paraffins of greater than or equal to 75 wt.

%, greater than or equal to 80 wt. %, greater than or equal to 85 wt. %, greater than or equal to 90 wt. %, greater than or equal to 95 wt. %, or even greater than or equal to 98 wt. % based on the total weight of the converted effluent 116. In embodiments, the converted effluent may comprise from 75 wt. % to 100 wt. %, from 75 wt. % to 99 wt. %, from 75 wt. % to 98 wt. %, from 75 wt. % to 95 wt. %, from 8 wt. % to 90 wt. %, from 80 wt. % to 100 wt. %, from 80 wt. % to 99 wt. %, from 80 wt. % to 98 wt. %, from 80 wt. % to 95 wt. %, from 80 wt. % to 90 wt. %, from 85 wt. % to 100 wt. %, from 85 wt. % to 99 wt. %, from 85 wt. % to 98 wt. %, from 85 wt. % to 95 wt. %, from 85 wt. % to 90 wt. %, from 90 wt. % to 100 wt. %, from 90 wt. % to 99 wt. %, from 90 wt. % to 98 wt. %, from 90 wt. % to 95 wt. %, from 95 wt. % to 100 wt. %, from 95 wt. % to 99 wt. %, from 95 wt. % to 98 wt. %, or from 98 wt. % to 100 wt. % paraffin compounds based on the total weight of the converted effluent 116.

Referring now to FIG. 2, in embodiments, the system 100 may include a converted effluent separation system 200 disposed directly downstream of the naphthene conversion unit 110. The converted effluent 116 may be passed from the naphthene conversion unit 110 directly to the converted effluent separation system 200. The converted effluent separation system 200 may include one or a plurality of separation units, which may separate the converted effluent 116 to produce at least a light gas effluent 204, a light naphtha 212, and a heavy naphtha 214. In embodiments, the converted effluent separation system 200 may further separate the converted effluent 116 to produce a C3-C4 effluent 206.

In embodiments, the converted effluent separation system 200 may comprise a light ends removal unit 202 and a naphtha separation unit 210 downstream of the light ends removal unit 202. The light ends removal unit 202 may be operable to separate the light hydrocarbons and gases from the converted effluent 116. The light gases may include excess hydrogen from the naphthene conversion unit 110, and the light hydrocarbons may include C1-C2 hydrocarbons, such as but not limited to methane, ethane, ethylene, or combinations of these. In embodiments, the light ends removal unit 202 may further separate a C3-C4 effluent 206 from the converted effluent 116. The C3-C4 effluent 206 may comprise hydrocarbons having 3-4 carbon atoms, such as mixed butanes, mixed butenes, propane, propene, or combinations of these, from the converted effluent 116. The light ends removal unit 202 may be operated at a pressure of the overhead (light gas stream 204) of from 500 kPa (5 bar) to 2,000 kPa (20 bar). The pressure may depend on the desired recovery of the C3-C4 effluent 206.

The remaining C5+ constituents may be passed on to the naphtha separation unit 210 in the C5+ stream 208. The naphtha separation unit 210 may separate the C5+ stream 208 into a light naphtha 212 and a heavy naphtha 214. In embodiments, the naphtha separation unit 210 may be a splitter unit operable to separate the C5+ stream 208 into the light naphtha 212 and the heavy naphtha 214 through boiling point differences. In embodiments, a C5+ slip stream 209 may be drawn off between the light ends removal unit 202 and the naphtha separation unit 210 and passed on to the steam cracker 150.

The light gas stream 204 may comprise hydrogen and C1 to C2 hydrocarbons, such as but not limited to methane, ethane, ethylene, or combinations of these. The light gas stream 204 may comprise greater than or equal to 90%, greater than or equal to 95%, greater than or equal to 98%, or even greater than or equal to 99% of the hydrogen and C1-C2 hydrocarbons from the converted effluent 116. The light gas stream 204 may be passed out of the system 100 to one or more downstream treatment units, such as hydrogen recovery and recycle, further separation, fuel gas, or other downstream process. In embodiments, any off gas comprising of methane and hydrogen can be sent to PSA for hydrogen recovery or directly used as fuel.

The C3-C4 effluent 206 may include hydrocarbons having 3-4 carbon atoms, such as but not limited to propane, propylene, n-butane, isobutane, butene, isobutene, or combinations of these. In embodiments, the C3-C4 effluent 206 may include greater than or equal to 75%, greater than or equal to 80%, greater than or equal to 85%, greater than or equal to 90%, greater than or equal to 95%, greater than or equal to 98%, or even greater than or equal to 99% of the C3-C4 hydrocarbons from the converted effluent 116. The C3-C4 effluent 206 may be passed on to the paraffin separation system 130 of the reverse isomerization system 120 or may be passed to a debutanizer system 250 for separation of the C3-C4 effluent 206 into a C3 product stream, a normal butane stream, and an isobutane stream, as will be discussed in greater detail in the present disclosure. In some embodiments, the C2-C4 paraffins separated from the converted effluent 116 may be passed to a mixed feed steam cracker (not shown).

Referring again to FIG. 2, as previously discussed, the naphtha separation unit 210 may separate the C5+ stream 208 into the light naphtha 212 and the heavy naphtha 214. The light naphtha 212 may comprise C5 and C6 constituents from the converted effluent 116. The C5 and C6 constituents include, but are not limited to, normal pentane, isopentanes, hexane, isohexanes, and combinations of these. In embodiments, the light naphtha 212 may comprise at least 75%, at least 80%, at least 85%, at least 90%, at least 95%, at least 98%, or even at least 99% of the C5-C6 constituents from the converted effluent 116. The light naphtha 212 may be passed from the naphtha separation unit 210 to the reverse isomerization system 120, such as to the paraffin separation system 130 of the reverse isomerization system 120. In the paraffin separation system 130, the light naphtha 212, along with the isomerate from the reverse isomerization unit, may be separated in one or more isoparaffin-rich streams and one or more normal paraffin-rich streams, as will be discussed in greater detail in the present disclosure.

The heavy naphtha 214 may comprise the hydrocarbons from the converted effluent 116 having greater than or equal to 7 carbon atoms (C7+). The heavy naphtha 214 may have at least 75%, at least 80%, at least 85%, at least 90%, at least 95%, at least 98%, or even at least 99% of the C7+ hydrocarbons from the converted effluent 116. In embodiments, the heavy naphtha 214 may be passed from the naphtha separation unit 210 directly to the steam cracker 150. In embodiments, at least a portion of or all of the heavy naphtha 214 may be passed to gasoline blending or to a catalytic reforming unit for quality improvement, such as but not limited increasing the octane number of the heavy naphtha 214.

Referring again to FIG. 1, at least a portion of or all of the converted effluent 116 may be passed to the reverse isomerization system 120 downstream of the naphthene conversion unit 110. In embodiments, only a portion of the converted effluent 116, such as but not limited to the light naphtha 212 (FIG. 2), may be passed to the reverse isomerization system 120. In embodiments, the butane-containing stream 108 may also be passed to the reverse isomerization system 120. Referring to FIG. 1, the reverse isomerization system 120 may comprise a paraffin separation system 130 and a reverse isomerization unit 140 disposed downstream of the paraffin separation system 130. The paraffin separation system 130 may operate to separate the converted effluent 116 (or portion of the converted effluent 116), the butane-containing stream 108, or both to produce at least one isoparaffin-rich stream 134 and at least one n-paraffin-rich stream 136. The reverse isomerization unit 140 may be operable to isomerize isoparaffins from the isoparaffin-rich stream 134 to produce an isomerate 144 having an equilibrium mixture of isoparaffins and normal paraffins. The isomerate 144 may then be passed back to the paraffin separation system 130 for separation of the isomerate 144 to produce the at least one isoparaffin-rich stream 134 and the at least one n-paraffin-rich stream 136. The process scheme of the reverse isomerization system 120 enables the feed to the reverse isomerization reactor 140 to be highly rich in isoparaffins, which may maximize the approach to equilibrium.

Referring again to FIG. 1, in embodiments, the paraffin separation system 130 may receive at least a portion of the converted effluent 116, the butane-containing stream 108, the isomerate 144, or combinations of these and separate these input streams to produce a light gas stream 132, the at least one isoparaffin-rich stream 134, and the at least one n-paraffin-rich stream 136. The paraffin separation system 130 may include one or a plurality of separation units operable to separate the portion of the converted effluent 116, butane-containing stream 108, or both to produce the at least one isoparaffin-rich stream 134 and at least one n-paraffin-rich stream. The separation units of the paraffin separation system 130 may include a plurality of fractionation columns (FIG. 2), one or more divided wall fractionation columns (FIG. 3), one or more adsorption separation units (FIG. 4), depropanizers, debutanizers, gas liquid separators, other separation units, or combinations of these. When the paraffin separation system 130 comprises a plurality of separation units, the plurality of separation units may be arranged in parallel, in series, or a combination of parallel and in series separation units.

Referring again to FIG. 1, the light gas stream 132 may include any hydrogen from the naphthene conversion unit 110 and any hydrocarbons having from 1 to 3 carbon atoms. The light gas stream 132 may be a plurality of light gas streams, such as but not limited to, a propane stream, a stream comprising hydrogen and C1-C2 hydrocarbons, or combinations of these. The light gas stream 132 may be passed out of the system to one or more processing units, such as but not limited to hydrogen recovery, hydrocarbon recovery, fuel gas, or other process unit.

The n-paraffin-rich stream 136 may comprise primarily normal paraffins, which refer to straight chain paraffins with no branching. In embodiments, the n-paraffin-rich stream 136 may comprise normal paraffins having from 4 to 12 carbon atoms. Referring to FIG. 2, in embodiments in which only the light naphtha 212 portion of the converted effluent 116 is passed to the paraffin separation system 130, then the n-paraffin-rich stream 136 may comprise normal paraffins having from 4 to 6 carbon atoms, such as n-butane, n-pentane, n-hexane, or combinations of these. In embodiments, the n-paraffin-rich stream 136 may include a plurality of n-paraffin-rich streams, such as but not limited to, an n-butane stream 256, an n-pentane stream 174, an n-hexane stream 178, or combinations of these. In embodiments, the at least one n-paraffin-rich stream 136 may comprise at least 80%, at least 90%, at least 95%, at least 98%, or at least 99% of the normal paraffins having greater than or equal to 4 carbon atoms from the input streams to the paraffin separation system 130.

Referring again to FIG. 1, the n-paraffin-rich stream 136 may also include at least some isoparaffins, however, the concentration of n-paraffins in the n-paraffin-rich stream 136 is greater than the concentration of isoparaffins in the n-paraffin-rich stream 136. The at least one n-paraffin-rich stream 136 may have less than or equal to 20 wt. %, less than or equal to 5 wt. %, or even less than or equal to 1 wt. % isoparaffins based on the total weight of the n-paraffin-rich stream 136. In embodiments, the at least one n-paraffin-rich stream 136 may comprise from 0 (zero) wt. % to 20 wt. %, from 0 wt. % to 5 wt. %, from 0 wt. % to 1 wt. %, from 0.001 wt. % to 20 wt. %, from 0.001 wt. % to 5 wt. %, from 0.001 wt. % to 1 wt. %, from 0.1 wt. % to 20 wt. %, from 0.1 wt. % to 5 wt. %, from 0.1 wt. % to 1 wt. %, from 1 wt. % to 20 wt. %, or from 1 wt. % to 5 wt. % isoparaffins based on the total weight of the n-paraffin-rich stream 136. In embodiments, the n-paraffin-rich stream 136 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % normal paraffins based on the total weight of the n-paraffin-rich stream 136. The n-paraffin-rich stream 136 may be passed from the paraffin separation system 130 to the steam cracker 150 for steam cracking to produce ethylene.

Referring again to FIG. 1, the isoparaffin-rich stream 134 may comprise primarily isoparaffins, which refer to branched paraffins. In embodiments, the isoparaffin-rich stream 134 may comprise isoparaffins having from 4 to 12 carbon atoms. Referring to FIG. 2, in embodiments in which only the light naphtha 212 portion of the converted effluent 116 is passed to the paraffin separation system 130, then the isoparaffin-rich stream 134 may comprise isoparaffins having from 4 to 6 carbon atoms, such as isobutane, isopentanes, isohexanes, or combinations of these. In embodiments, the isoparaffin-rich stream 134 may include a plurality of isoparaffin-rich streams, such as but not limited to, an isobutane stream 254, a C5 isoparaffin stream 162, a C6 isoparaffin stream 172, or combinations of these. In embodiments, the at least one isoparaffin-rich stream 134 may comprise at least 80%, at least 90%, at least 95%, at least 98%, or at least 99% of the isoparaffins having greater than or equal to 4 carbon atoms present in the collection of input streams to the paraffin separation system 130.

Referring again to FIG. 1, the isoparaffin-rich stream 134 may also include at least some normal paraffins, however, the concentration of isoparaffins in the isoparaffin-rich stream 134 is greater than the concentration of normal paraffins in the isoparaffin-rich stream 134. The concentration of isoparaffins in the isoparaffin-rich stream 134 is greater than a concentration of isoparaffins in an equilibrium mixture of isoparaffins and normal paraffins. The at least one isoparaffin-rich stream 134 may have less than or equal to 20 wt. %, less than or equal to 5 wt. %, or even less than or equal to 1 wt. % normal paraffins based on the total weight of the isoparaffin-rich stream 134. In embodiments, the at least one isoparaffin-rich stream 134 may comprise from 0 (zero) wt. % to 20 wt. %, from 0 wt. % to 5 wt. %, from 0 wt. % to 1 wt. %, from 0.001 wt. % to 20 wt. %, from 0.001 wt. % to 5 wt. %, from 0.001 wt. % to 1 wt. %, from 0.1 wt. % to 20 wt. %, from 0.1 wt. % to 5 wt. %, from 0.1 wt. % to 1 wt. %, from 1 wt. % to 20 wt. %, or from 1 wt. % to 5 wt. % normal paraffins based on the total weight of the isoparaffin-rich stream 134. In embodiments, the isoparaffin-rich stream 134 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % isoparaffins based on the total weight of the isoparaffin-rich stream 134. The isoparaffin-rich stream 134 may be passed from the paraffin separation system 130 to the reverse isomerization unit 140.

Referring now to FIG. 2, in embodiments, the paraffin separation system 130 may comprise a two-stage fractionation system operable to separate the light naphtha 212 and at least a portion of or all of the isomerate 144 to produce a plurality of n-paraffin streams and a plurality of isoparaffin streams. The system 100 may further include a debutanizer system 250 for separating the butane-containing stream 108, the C3-C4 effluent 206 recovered from the converted effluent separation system 200, LPG stream 109, other C4-streams, and combinations of these streams to produce at least an isobutane stream 254 and an n-butane stream 256. The system 100 may further include an isomerate separator 230 operable to separate hydrogen and C1-C4 hydrocarbon gases from the isomerate 144 upstream of the paraffin separation system 130.

Referring to FIG. 2, the two-stage fractionation system may include a first fractionation column 160 and a second fractionation column 170 downstream of the first fractionation column 160. The light naphtha 212 may be passed from the converted effluent separation system 130 to the first fractionation column 160. Additionally, at least a portion of the isomerate 144, such as the C5+ isomerate effluent 236 from the isomerate separator 230, may be passed to the first fractionation column 160. The first fractionation column 160 may separate the light naphtha 212 and the portion of the isomerate 144 to produce at least a C5 isoparaffin stream 162 and a bottom stream 164.

The C5 isoparaffin stream 162 may be rich in isoparaffins having 5 carbon atoms, which are referred to in the present disclosure as C5 isoparaffins. In embodiments, the C5 isoparaffin stream 162 may comprise at least 75%, at least 80%, at least 85%, at least 90%, at least 95%, at least 98%, or even at least 99% of the C5 isoparaffins from the light naphtha 212, the portion of the isomerate 144, or both. In embodiments, the C5 isoparaffin stream 162 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % C5 isoparaffins based on the total weight of the C5 isoparaffin stream 162.

In embodiments, the C5 isoparaffin stream 162 may have less than or equal to 20 wt. %, less than or equal to 5 wt. %, or even less than or equal to 1 wt. % normal paraffins based on the total weight of the C5 isoparaffin stream 162. In embodiments, the C5 isoparaffin stream 162 may comprise from 0 (zero) wt. % to 20 wt. %, from 0 wt. % to 5 wt. %, from 0 wt. % to 1 wt. %, from 0.001 wt. % to 20 wt. %, from 0.001 wt. % to 5 wt. %, from 0.001 wt. % to 1 wt. %, from 0.1 wt. % to 20 wt. %, from 0.1 wt. % to 5 wt. %, from 0.1 wt. % to 1 wt. %, from 1 wt. % to 20 wt. %, or from 1 wt. % to 5 wt. % normal paraffins based on the total weight of the C5 isoparaffin stream 162. The C5 isoparaffin stream 162 may be passed to the reverse isomerization unit 140 or combined with other isoparaffin streams (C6 isoparaffin stream 172, isobutane stream 254, or both) upstream of the isomerization unit 140.

The bottom stream 164 may comprise normal paraffins having 5 or more carbon atoms and isoparaffins having 6 carbon atoms. Throughout the present disclosure, isoparaffins having 6 carbon atoms will be referred to as C6 isoparaffins, normal paraffins having 5 carbon atoms will be referred to as C5 n-paraffins, and normal paraffins having 6 carbon atoms will be referred to as C6 n-paraffins. The bottom stream 164 may comprise at least 75%, at least 80%, at least 85%, at least 90%, at least 95%, at least 98%, or even at least 99% of the C6 isoparaffins and C5+ normal paraffins from the light naphtha 212, the portion of the isomerate 144, or both. In embodiments, the bottom stream 164 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % C6 isoparaffins and C5+ normal paraffins based on the total weight of the bottom stream 164. The bottom stream 164 may also include any C5 isoparaffins not separated out into the C5 isoparaffin stream 162.

The bottom stream 164 may be passed from the first fractionation column 160 to the second fractionation column 170. In embodiments, all of the bottom stream 164 may be passed directly from the first fractionation column 160 to the second fractionation column 170. The second fractionation column 170 may separate the bottom stream 164 from the first fractionation column 160 to produce at least a C6 isoparaffin stream 172 and one or more normal paraffin stream. The normal paraffin streams may include a C5 n-paraffin stream 174, a C6 n-paraffin stream 176, or a combination of these. Additionally, the second fractionation column 170 may produce a drag stream 178.

The C6 isoparaffin stream 172 may be rich in C6 isoparaffins. In embodiments, the C6 isoparaffin stream 172 may comprise at least 75%, at least 80%, at least 85%, at least 90%, at least 95%, at least 98%, or even at least 99% of the C6 isoparaffins from the bottom stream 164. In embodiments, the C6 isoparaffin stream 172 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % C6 isoparaffins based on the total weight of the C6 isoparaffin stream 172. The C6 isoparaffin stream 172 may be passed to the reverse isomerization unit 140 or combined with other isoparaffin streams (C5 isoparaffin stream 162, isobutane stream 254, or both) upstream of the isomerization unit 140.

The C5 n-paraffin stream 174 may comprise primarily C5 n-paraffins. In embodiments, the C5 n-paraffin stream 174 may comprise at least 80%, at least 90%, at least 95%, at least 98%, or at least 99% of the C5 n-paraffins from the bottom stream 164. In embodiments, the C5 n-paraffin stream 174 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % C5 n-paraffins based on the total weight of the C5 n-paraffin stream 174. The C5 n-paraffin stream 174 may comprise at least some isoparaffins, however, the concentration of C5 n-paraffins is greater than the concentration of isoparaffins in the C5 n-paraffin stream 174. In embodiments, the C5 n-paraffin stream 174 may have less than or equal to 20 wt. %, less than or equal to 5 wt. %, or even less than or equal to 1 wt. % isoparaffins based on the total weight of the C5 n-paraffin stream 174. In embodiments, the C5 n-paraffin stream 174 may comprise from 0 (zero) wt. % to 20 wt. %, from 0 wt. % to 5 wt. %, from 0 wt. % to 1 wt. %, from 0.001 wt. % to 20 wt. %, from 0.001 wt. % to 5 wt. %, from 0.001 wt. % to 1 wt. %, from 0.1 wt. % to 20 wt. %, from 0.1 wt. % to 5 wt. %, from 0.1 wt. % to 1 wt. %, from 1 wt. % to 20 wt. %, or from 1 wt. % to 5 wt. % isoparaffins based on the total weight of the C5 n-paraffin stream 174. The C5 n-paraffin stream 174 may be passed from the second fractionation column 170 to the steam cracker 150 for steam cracking to produce ethylene.

The C6 n-paraffin stream 176 may comprise primarily normal paraffins having 6 carbon atoms (C6 n-paraffins) and any normal paraffins having greater than 6 carbon atoms. In embodiments, the C6 n-paraffin stream 176 may comprise at least 80%, at least 90%, at least 95%, at least 98%, or at least 99% of the C6 n-paraffins from the bottom stream 164. In embodiments, the C6 n-paraffin stream 176 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % C6 n-paraffins based on the total weight of the C6 n-paraffin stream 176. The C6 n-paraffin stream 176 may comprise at least some isoparaffins, however, the concentration of C6 n-paraffins is greater than the concentration of isoparaffins in the C6 n-paraffin stream 176. In embodiments, the C6 n-paraffin stream 176 may have less than or equal to 20 wt. %, less than or equal to 5 wt. %, or even less than or equal to 1 wt. % isoparaffins based on the total weight of the C6 n-paraffin stream 176. In embodiments, the C6 n-paraffin stream 176 may comprise from 0 (zero) wt. % to 20 wt. %, from 0 wt. % to 5 wt. %, from 0 wt. % to 1 wt. %, from 0.001 wt. % to 20 wt. %, from 0.001 wt. % to 5 wt. %, from 0.001 wt. % to 1 wt. %, from 0.1 wt. % to 20 wt. %, from 0.1 wt. % to 5 wt. %, from 0.1 wt. % to 1 wt. %, from 1 wt. % to 20 wt. %, or from 1 wt. % to 5 wt. % isoparaffins based on the total weight of the C6 n-paraffin stream 176. The C6 n-paraffin stream 176 may be passed from the second fractionation column 170 to the steam cracker 150 for steam cracking to produce ethylene.

In embodiments, an optional drag stream 178 may be produced by the second fractionation column 170 and passed to the steam cracker 150 or passed out of the system 100, such as but not limited to passing the drag stream 178 to the gasoline pool or other hydrocarbon conversion unit, such as fluidized catalytic cracking process or hydrocracking process. The drag stream 178 may reduce or prevent build-up of isoparaffins in the reverse isomerization system 120.

Figure 3:
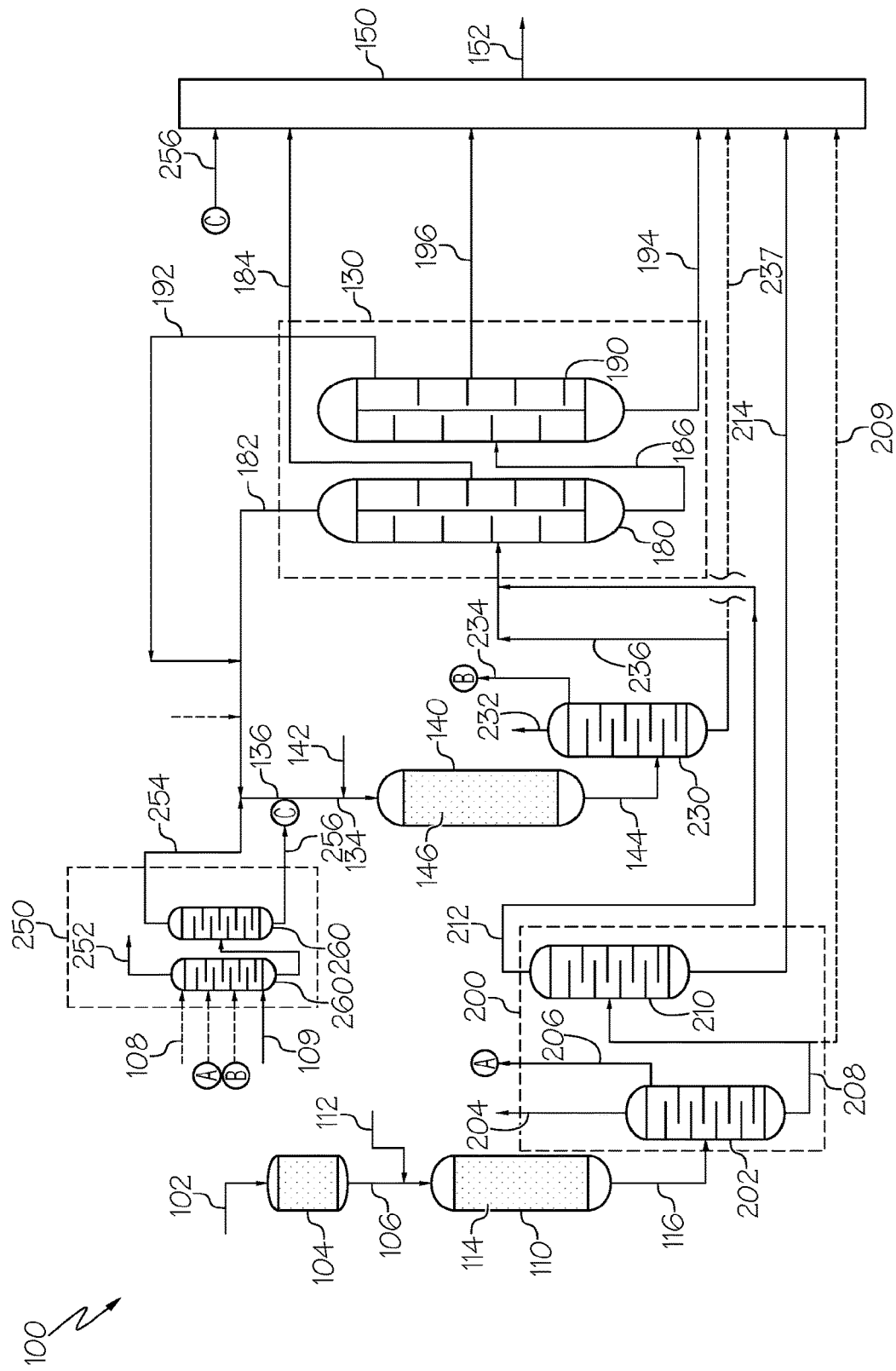
FIG. 3 schematically depicts a generalized flow diagram of still another system for upgrading a naphtha feed, including desulfurizing the naphtha feed, according to one or more embodiments shown and described in this disclosure.

Referring now to FIG. 3, in embodiments, the paraffin separation system 130 may comprise a two-stage divided wall column system. In embodiments, the paraffin separation system 130 may comprise a first divided wall fractionation column 180 and a second divided wall fractionation column 190 disposed downstream of the first divided wall fractionation column 180. The use of divided wall fractionation columns may improve separation efficiency and reduce the operating costs by reducing the amount of energy required compared to conventional distillation columns. In particular, each of the divided-wall fractionation columns can produce 3 high-purity product streams simultaneously.

The light naphtha 212 may be passed from the converted effluent separation system 130 to the first divided-wall fractionation column 180. Additionally, at least a portion of the isomerate 144, such as the C5+ isomerate effluent 236 from the isomerate separator 230, may be passed to the first divided-wall fractionation column 180. The first divided-wall fractionation column 180 may separate the light naphtha 212 and the portion of the isomerate 144 to produce at least a C5 isoparaffin stream 182, a C5 n-paraffin stream 184, and a C6+ bottom stream 186.

The C5 isoparaffin stream 182 may be rich in C5 isoparaffins. In embodiments, the C5 isoparaffin stream 182 may comprise at least 75%, at least 80%, at least 85%, at least 90%, at least 95%, at least 98%, or even at least 99% of the C5 isoparaffins from the light naphtha 212, the portion of the isomerate 144, or both. In embodiments, the C5 isoparaffin stream 182 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % C5 isoparaffins based on the total weight of the C5 isoparaffin stream 182. In embodiments, the C5 isoparaffin stream 182 may have less than or equal to 20 wt. %, less than or equal to 5 wt. %, or even less than or equal to 1 wt. % normal paraffins based on the total weight of the C5 isoparaffin stream 182. In embodiments, the C5 isoparaffin stream 182 may comprise from 0 (zero) wt. % to 20 wt. %, from 0 wt. % to 5 wt. %, from 0 wt. % to 1 wt. %, from 0.001 wt. % to 20 wt. %, from 0.001 wt. % to 5 wt. %, from 0.001 wt. % to 1 wt. %, from 0.1 wt. % to 20 wt. %, from 0.1 wt. % to 5 wt. %, from 0.1 wt. % to 1 wt. %, from 1 wt. % to 20 wt. %, or from 1 wt. % to 5 wt. % normal paraffins based on the total weight of the C5 isoparaffin stream 182. The C5 isoparaffin stream 182 may be passed to the reverse isomerization unit 140 or combined with other isoparaffin streams (C6 isoparaffin stream 192, isobutane stream 254, or both) upstream of the isomerization unit 140.

Referring again to FIG. 3, the C5 n-paraffin stream 184 may comprise primarily C5 n-paraffins. In embodiments, the C5 n-paraffin stream 184 may comprise at least 80%, at least 90%, at least 95%, at least 98%, or at least 99% of the C5 n-paraffins from the light naphtha 212, the portion of the isomerate 144, or both. In embodiments, the C5 n-paraffin stream 184 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % C5 n-paraffins based on the total weight of the C5 n-paraffin stream 184. The C5 n-paraffin stream 184 may comprise at least some isoparaffins, however, the concentration of C5 n-paraffins is greater than the concentration of isoparaffins in the C5 n-paraffin stream 184. In embodiments, the C5 n-paraffin stream 184 may have less than or equal to 20 wt. %, less than or equal to 5 wt. %, or even less than or equal to 1 wt. % isoparaffins based on the total weight of the C5 n-paraffin stream 184. In embodiments, the C5 n-paraffin stream 184 may comprise from 0 (zero) wt. % to 20 wt. %, from 0 wt. % to 5 wt. %, from 0 wt. % to 1 wt. %, from 0.001 wt. % to 20 wt. %, from 0.001 wt. % to 5 wt. %, from 0.001 wt. % to 1 wt. %, from 0.1 wt. % to 20 wt. %, from 0.1 wt. % to 5 wt. %, from 0.1 wt. % to 1 wt. %, from 1 wt. % to 20 wt. %, or from 1 wt. % to 5 wt. % isoparaffins based on the total weight of the C5 n-paraffin stream 184. The C5 n-paraffin stream 184 may be passed from the first divided-wall fractionation column 180 to the steam cracker 150 for steam cracking to produce ethylene.

The C6+ bottom stream 186 may comprise iso and normal paraffins having 6 or more carbon atoms. The C6+ bottom stream 186 may comprise at least 75%, at least 80%, at least 85%, at least 90%, at least 95%, at least 98%, or even at least 99% of the C6+ paraffin compounds (C6+ isoparaffins and C6+ normal paraffins) from the light naphtha 212, the portion of the isomerate 144, or both. In embodiments, the C6+ bottom stream 186 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % C6+ paraffin compounds based on the total weight of the C6+ bottom stream 186. The C6+ bottom stream 186 may also include any C5 paraffin compounds not separated out into the C5 isoparaffin stream 182, the C5 n-paraffin stream 184, or both.

The C6+ bottom stream 186 may be passed from the first divided-wall fractionation column 180 to the second divided-wall fractionation column 190. In embodiments, all of the C6+ bottom stream 186 may be passed directly from the first divided-wall fractionation column 180 to the second divided-wall fractionation column 190. The second divided-wall fractionation column 190 may separate the C6+ bottom stream 186 to produce at least a C6 isoparaffin stream 192 and a C6 n-paraffin stream 194. Additionally, the second divided-wall fractionation column 190 may produce a drag stream 196.

The C6 isoparaffin stream 192 may be rich in C6 isoparaffins. In embodiments, the C6 isoparaffin stream 192 may comprise at least 75%, at least 80%, at least 85%, at least 90%, at least 95%, at least 98%, or even at least 99% of the C6 isoparaffins from the C6+ bottom stream 186. In embodiments, the C6 isoparaffin stream 192 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % C6 isoparaffins based on the total weight of the C6 isoparaffin stream 192. The C6 isoparaffin stream 192 may be passed to the reverse isomerization unit 140 or combined with other isoparaffin streams (C5 isoparaffin stream 182, isobutane stream 254, or both) upstream of the isomerization unit 140.

The C6 n-paraffin stream 194 may comprise primarily normal paraffins having 6 carbon atoms (C6 n-paraffins) and any normal paraffins having greater than 6 carbon atoms. In embodiments, the C6 n-paraffin stream 194 may comprise at least 80%, at least 90%, at least 95%, at least 98%, or at least 99% of the C6 n-paraffins from the C6+ bottom stream 186. In embodiments, the C6 n-paraffin stream 194 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % C6 n-paraffins based on the total weight of the C6 n-paraffin stream 194. The C6 n-paraffin stream 194 may comprise at least some isoparaffins, however, the concentration of C6 n-paraffins is greater than the concentration of isoparaffins in the C6 n-paraffin stream 194. In embodiments, the C6 n-paraffin stream 194 may have less than or equal to 20 wt. %, less than or equal to 5 wt. %, or even less than or equal to 1 wt. % isoparaffins based on the total weight of the C6 n-paraffin stream 194. In embodiments, the C6 n-paraffin stream 194 may comprise from 0 (zero) wt. % to 20 wt. %, from 0 wt. % to 5 wt. %, from 0 wt. % to 1 wt. %, from 0.001 wt. % to 20 wt. %, from 0.001 wt. % to 5 wt. %, from 0.001 wt. % to 1 wt. %, from 0.1 wt. % to 20 wt. %, from 0.1 wt. % to 5 wt. %, from 0.1 wt. % to 1 wt. %, from 1 wt. % to 20 wt. %, or from 1 wt. % to 5 wt. % isoparaffins based on the total weight of the C6 n-paraffin stream 194. The C6 n-paraffin stream 194 may be passed from the second divided-wall fractionation column 190 to the steam cracker 150 for steam cracking to produce ethylene.

In embodiments, an optional drag stream 196 may be produced by the second divided-wall fractionation column 190 and passed to the steam cracker 150. The drag stream 196 may be produced and passed to the steam cracker 150 to reduce or prevent build-up of isoparaffins in the reverse isomerization system 120.

Figure 4:
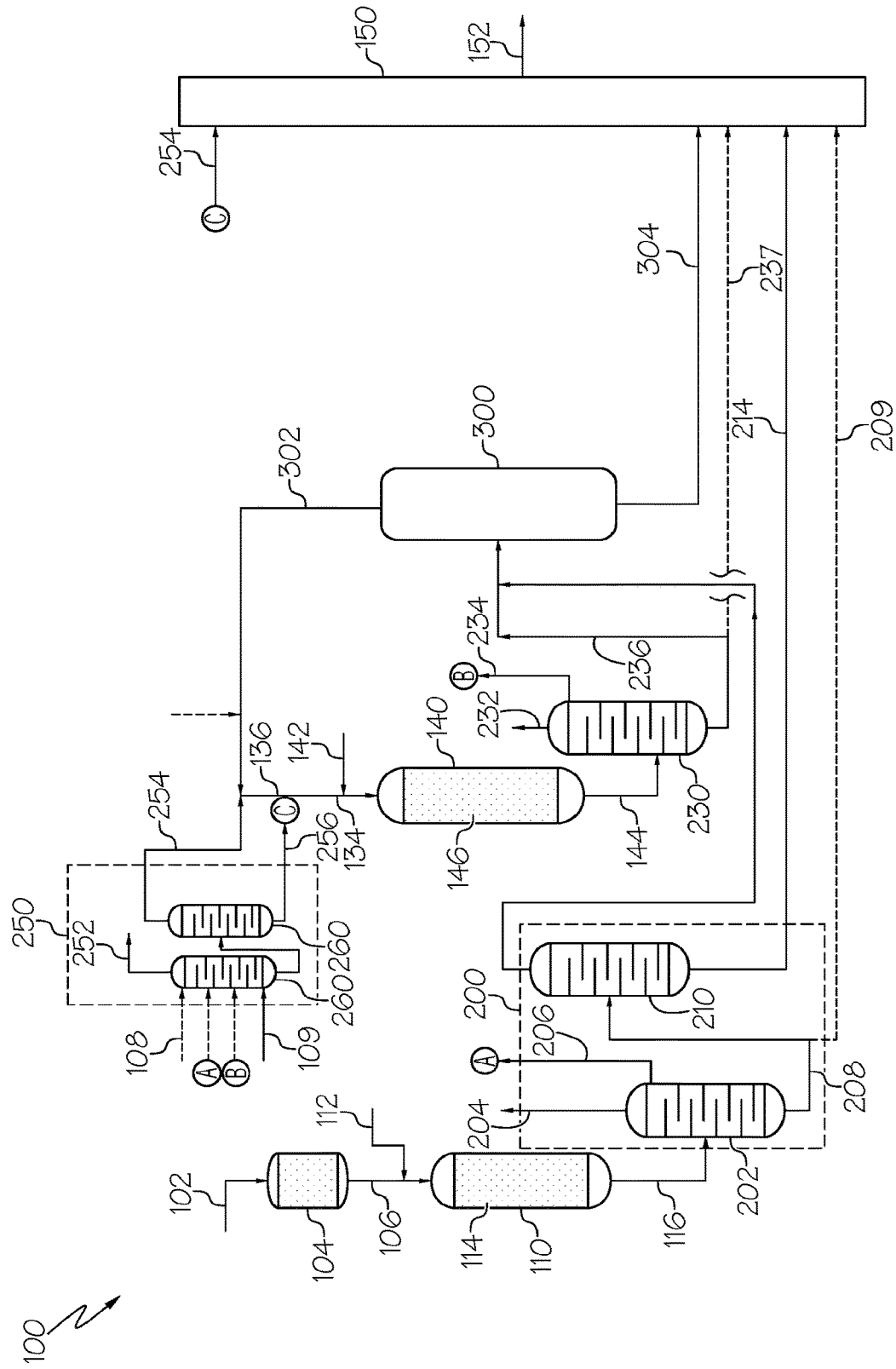
FIG. 4 schematically depicts a generalized flow diagram of another system for upgrading a naphtha feed, including desulfurizing the naphtha feed, according to one or more embodiments shown and described in this disclosure.

Referring now to FIG. 4, the paraffin separation system 130 may comprise an adsorption separation unit 300 for separating the paraffins into at least one isoparaffin stream and at least one n-paraffin stream. The light naphtha 212 may be passed from the converted effluent separation system 130 to the adsorption separation unit 300. Additionally, at least a portion of the isomerate 144, such as the C5+ isomerate effluent 236 from the isomerate separator 230, may be passed to the adsorption separation unit 300. The adsorption separation unit 300 may separate the light naphtha 212, the portion of the isomerate 144, or both to produce an isoparaffin-rich stream 302 and an n-paraffin-rich stream 304.

The adsorption separation unit 300 may comprise one or a plurality of adsorbent beds comprising molecular sieve adsorbents. The adsorption separation unit 300 may separate the mixed paraffin streams, such as the light naphtha 212, the portion of the isomerate 144, or both through difference on molecular size. Not intending to be bound by theory, the molecular sieve adsorbents may operate to adsorb molecules having a molecule size less than the pore size of the molecular sieve and to allow molecules having a molecule size greater than the pore size of the molecular sieve to pass by without being adsorbed. The molecular sieve adsorbents may be selected to adsorb normal paraffins and allow isoparaffins to pass through without adsorption into the pores. The normal paraffins may then be extracted from the adsorbent through a desorption cycle. In embodiments, the adsorption separation unit 300 may include a plurality of adsorbent beds so that one or more of the adsorbent beds can continue to separate the mixed paraffin streams to produce the isoparaffin-rich stream 302, while other of the plurality of adsorbent beds undergo a desorption cycle to produce the n-paraffin-rich stream 304.

Referring again to FIG. 4, the isoparaffin-rich stream 302 from the adsorption separation unit 300 may be rich in isoparaffins. In embodiments, the isoparaffin-rich stream 302 may comprise at least 75%, at least 80%, at least 85%, at least 90%, at least 95%, at least 98%, or even at least 99% of the isoparaffins from the light naphtha 212, the portion of the isomerate 144, or both. The isoparaffin-rich stream 302 can include C5 isoparaffins and C6 isoparaffins. The isoparaffin-rich stream 302 may also include any isoparaffins having greater than 6 carbon atoms. In embodiments, the isoparaffin-rich stream 302 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % isoparaffins based on the total weight of the isoparaffin-rich stream 302. The isoparaffin-rich stream 302 may include some n-paraffins. In embodiments, the isoparaffin-rich stream 302 may comprise less than or equal to 20 wt. %, less than or equal to 5 wt. %, or even less than or equal to 1 wt. % n-paraffins based on the total weight of the isoparaffin-rich stream 302. The isoparaffin-rich stream 302 may be passed to the reverse isomerization unit 140 or combined with other isoparaffin streams (isobutane stream 254) upstream of the isomerization unit 140.

The n-paraffin-rich stream 304 may comprise primarily normal paraffins having greater than or equal to 5 carbon atoms (C5+n-paraffins). In embodiments, the n-paraffin-rich stream 304 may comprise at least 80%, at least 90%, at least 95%, at least 98%, or at least 99% of the n-paraffins from the light naphtha 212, the portion of the isomerate 144 or both. In embodiments, the n-paraffin-rich stream 304 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % n-paraffins based on the total weight of the n-paraffin-rich stream 304. The n-paraffin-rich stream 304 may comprise at least some isoparaffins, however, the concentration of n-paraffins is greater than the concentration of isoparaffins in the n-paraffin-rich stream 304. In embodiments, the n-paraffin-rich stream 304 may have less than or equal to 20 wt. %, less than or equal to 5 wt. %, or even less than or equal to 1 wt. % isoparaffins based on the total weight of the n-paraffin-rich stream 304. In embodiments, the n-paraffin-rich stream 304 may comprise from 0 (zero) wt. % to 20 wt. %, from 0 wt. % to 5 wt. %, from 0 wt. % to 1 wt. %, from 0.001 wt. % to 20 wt. %, from 0.001 wt. % to 5 wt. %, from 0.001 wt. % to 1 wt. %, from 0.1 wt. % to 20 wt. %, from 0.1 wt. % to 5 wt. %, from 0.1 wt. % to 1 wt. %, from 1 wt. % to 20 wt. %, or from 1 wt. % to 5 wt. % isoparaffins based on the total weight of the n-paraffin-rich stream 304. The n-paraffin-rich stream 304 may be passed from the adsorption separation unit 300 to the steam cracker 150 for steam cracking to produce ethylene.

Referring again to FIG. 2, in embodiments, the system 100 may comprise a debutanizer system 250 for separating the butane-containing stream 108 upstream of the reverse isomerization system 120. The debutanizer system 250 may be a separation system operable to separate the butane-containing stream 108 to produce an isobutane stream 254 and an n-butane stream 256. The debutanizer system 250 may be operable to receive the butane-containing stream 108. The debutanizer system 250 may be operable to receive one or more LPG streams 109. In embodiments, an inlet of the debutanizer system 250 may be fluidly coupled to an outlet of the light ends removal unit 202 the isomerate separator 230, or both so that the C3-C4 effluent 206, C3-C4 isomerate effluent 234, or both can be passed to and separated in the debutanizer system 250. The butane-containing stream 108, any LPG streams 109, the C3-C4 effluent 206, the C3-C4 isomerate effluent 234, or combinations of these may be passed directly to the debutanizer system 250 or combined upstream of the debutanizer system 250.

The debutanizer system 250 may include one or a plurality of separation units operable to separate the butane-containing stream 108, any LPG streams 109, the C3-C4 effluent 206, the C3-C4 isomerate effluent 234, or combinations of these streams to produce a C3 product stream 252, an isobutane stream 154, and an n-butane stream 256. The C3 product stream 252 may include the constituents from the butane-containing stream 108, any LPG streams 109, the C3-C4 effluent 206, the C3-C4 isomerate effluent 234, or combinations of these streams having 3 carbons atoms or less than 3 carbons atoms. In particular, the C3 product stream 252 may comprise propane, propylene, or combinations of these.

The isobutane stream 254 may be rich in isobutane. In embodiments, the isobutane stream 154 may comprise at least 75%, at least 80%, at least 85%, at least 90%, at least 95%, at least 98%, or even at least 99% of the isobutane from the butane-containing stream 108, any LPG streams 109, the C3-C4 effluent 206, the C3-C4 isomerate effluent 234, or combinations of these streams. In embodiments, the isobutane stream 154 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % isobutane based on the total weight of the isobutane stream 254. The isobutane 254 may be passed to the reverse isomerization unit 140 or combined with other isoparaffin streams (C5 isoparaffin stream 162, 182, C6 isoparaffin stream 172, 192, or combinations of these streams) upstream of the isomerization unit 140.

The n-butane stream 256 may comprise primarily normal butane. In embodiments, the n-butane stream 256 may comprise at least 80%, at least 90%, at least 95%, at least 98%, or at least 99% of the n-butane from the butane-containing stream 108, any LPG streams 109, the C3-C4 effluent 206, the C3-C4 isomerate effluent 234, or combinations of these streams. In embodiments, the n-butane stream 256 may comprise from 80 wt. % to 100 wt. %, from 80 wt. % to 99.99 wt. %, from 80 wt. % to 99.9 wt. %, from 80 wt. % to 99 wt. %, from 90 wt. % to 100 wt. %, from 90 wt. % to 99.99 wt. %, from 90 wt. % to 99.9 wt. %, from 90 wt. % to 99 wt. %, from 95 wt. % to 100 wt. %, from 95 wt. % to 99.99 wt. %, from 95 wt. % to 99.9 wt. %, from 95 wt. % to 99 wt. %, from 98 wt. % to 100 wt. %, from 98 wt. % to 99.99 wt. %, from 98 wt. % to 99.9 wt. %, from 98 wt. % to 99 wt. %, or from 99 wt. % to 100 wt. % n-butane based on the total weight of the n-butane stream 256. The n-butane stream 256 may comprise at least some isoparaffins, however, the concentration of n-paraffins is greater than the concentration of isoparaffins in the n-butane stream 256. In embodiments, the n-butane stream 256 may have less than or equal to 20 wt. %, less than or equal to 5 wt. %, or even less than or equal to 1 wt. % isoparaffins based on the total weight of the n-butane stream 256. In embodiments, the n-butane stream 256 may comprise from 0 (zero) wt. % to 20 wt. %, from 0 wt. % to 5 wt. %, from 0 wt. % to 1 wt. %, from 0.001 wt. % to 20 wt. %, from 0.001 wt. % to 5 wt. %, from 0.001 wt. % to 1 wt. %, from 0.1 wt. % to 20 wt. %, from 0.1 wt. % to 5 wt. %, from 0.1 wt. % to 1 wt. %, from 1 wt. % to 20 wt. %, or from 1 wt. % to 5 wt. % isoparaffins based on the total weight of the n-butane stream 256. The n-butane stream 256 may be passed from the debutanizer system 250 to the steam cracker 150 for steam cracking to produce ethylene.

Referring again to FIG. 1, in embodiments, the isoparaffin-rich stream 134 may be passed to the reverse isomerization unit 140. The isoparaffin-rich stream 134 may include any one or more of the isoparaffin-rich streams previously described in the present disclosure, such as but not limited to the C5 isoparaffin stream 162 (FIG. 2), the C6 isoparaffin stream (FIG. 2), the C5 isoparaffin stream 182 (FIG. 3), the C5 isoparaffin stream 192 (FIG. 3), the isoparaffin-rich stream 302 from the adsorption separation unit 300 (FIG. 4), the isobutane stream 254 (FIGS. 2-4), or combinations of these isoparaffin-rich streams. Each of the isoparaffin-rich streams may be passed to the reverse isomerization unit 140 separately or may be combined upstream of the reverse isomerization unit 140 to produce a single isoparaffin-rich stream 134, which may then be fed to the reverse isomerization unit 140. Referring again to FIG. 2, in embodiments, the C5 isoparaffin stream 162, the C6 isoparaffin stream 172, the isobutane stream 254, or combinations of these streams may be passed directly to the reverse isomeraization unit 140 or may be combined upstream of the reverse isomerization unit 140 to produce the isoparaffin-rich stream 134. Referring to FIG. 3, in embodiments, the C5 isoparaffin stream 182, the C6 isoparaffin stream 192, the isobutane stream 254, or combinations of these streams may be passed directly to the reverse isomeraization unit 140 or may be combined upstream of the reverse isomerization unit 140 to produce the isoparaffin-rich stream 134. Referring now to FIG. 4, in embodiments, the isoparaffin-rich stream 302, the isobutane stream 254, or combinations of these streams may be passed directly to the reverse isomeraization unit 140 or may be combined upstream of the reverse isomerization unit 140 to produce the isoparaffin-rich stream 134. In embodiments, the isoparaffin-rich stream 134 fed to the reverse isomerization unit 140 may have a water content of less than or equal to 1 parts per million by weight.

Referring again to FIG. 1, hydrogen 142 may be passed to the reverse isomerization unit 140. The hydrogen 142 may be passed directly to the reverse isomerization unit 140 or combined with the isoparaffin-rich stream 134 upstream of the reverse isomerization unit 140. The hydrogen 142 can be supplied directly from the hydrogen header, such as from the make-up hydrogen gas compressor. In embodiments, the hydrogen 142 may be recovered hydrogen from a hydrocracker unit, such as from an amine scrubbed off gas from a flash drum of any hydrocracker unit. The hydrogen 142 may also include excess hydrogen recovered from the converted effluent 116 from the naphthene conversion unit 110, excess hydrogen recovered from the isomerate 144, or both.

Referring again to FIG. 1, the reverse isomerization unit 140 may be operable to isomerize at least a portion of the isoparaffin compounds from the isoparaffin-rich stream 134 to produce the isomerate 144, which may comprise an equilibrium mixture of isoparaffins and normal paraffins. In embodiments, the reverse isomerization unit 140 may be configured to contact the isoparaffin-rich stream 134 with the hydrogen 142 in the presence of the isomerization catalyst 146 at reaction conditions selected to isomerize at least a portion of the isoparaffins from the isoparaffin-rich stream 134 to produce an isomerate 144 having an equilibrium mixture of isoparaffins and normal paraffins.

The reverse isomerization unit 140 may include one or a plurality of isomerization reactors in series or in parallel. In embodiments, the reverse isomerization unit 140 may include multiple isomerization reactors arranged in series, such as in a lead-lag configuration. The isomerization reactors may be fixed-bed reactors, ebullated bed reactors, moving bed reactors, or combinations of these. In embodiments, the reverse isomerization unit 140 may comprise at least one isomerization reactor that is a fixed bed reactor. In embodiments, the isomerization reactor(s) of the reverse isomerization unit 130 may be a three phase reactor in which the hydrogen 142 is present in a gas phase, isoparaffin-rich stream 134 is in a liquid phase, and the isomerization catalyst 146 is in a solid phase. In embodiments, the isomerization reactor(s) of the reverse isomerization unit 140 may be a two-phase reactor where the hydrogen 142 is dissolved into the liquid phase comprising the isoparaffin-rich stream 134, and the isomerization catalyst 146 is in a solid phase.

The isomerization catalyst 146 in the isomerization reactors may comprise one or more catalyst metals supported on a catalyst support. The catalytic metals may be any metals in groups 8-10 of the International Union of Pure and Applied Chemistry (IUPAC) periodic table of elements. In embodiments, the catalyst metals may include one or more noble metals. Nobel metals can include but are not limited to gold, platinum, palladium, rhodium, ruthenium, osmium, or iridium. In embodiments, the catalytic metal may comprise one or more metals selected from the group consisting of iridium (Ir), platinum (Pt), palladium (Pd), rhodium (Rh), ruthenium (Ru), and combinations of these noble metals. In embodiments, the metals can be present as the pure metal compounds.

The catalyst support may be a chlorinated alumina, a sulfonated zirconium, a zeolite, or combinations of these. In embodiments, the catalyst support may be a chlorinated alumina. In embodiments, the catalyst support may be a zeolite, such as but not limited to an MOR zeolite, an MFI zeolite, a BEA zeolite, an FAU zeolite, or combinations of these zeolites.

The isomerization reactor(s) of the reverse isomerization unit 140 may be operated at conditions that promote isomerization of at least a portion of the isoparaffins from the isoparaffin-rich stream 134 to normal paraffins to produce the isomerate 144 comprising a mixture of isoparaffins and normal paraffins. The isomerization reactor(s) of the reverse isomerization unit 140 may be operated at an operating temperature of from 20° C. to 400° C., such as from 20° C. to 350° C., from 20° C. to 300° C., from 20° C. to 285° C., from 20° C. to 200° C., from 20° C. to 180° C., from 50° C. to 400° C., from 50° C. to 350° C., from 50° C. to 300° C., from 50° C. to 285° C., from 50° C. to 200° C., from 50° C. to 180° C., from 80° C. to 400° C., from 80° C. to 350° C., from 80° C. to 300° C., from 80° C. to 285° C., from 80° C. to 200° C., from 80° C. to 180° C., from 100° C. to 400° C., from 100° C. to 350° C., from 100° C. to 300° C., from 100° C. to 285° C., from 100° C. to 200° C., from 100° C. to 180° C., from 180 to 400° C., from 180° C. to 350° C., from 180° C. to 300° C., from 180° C. to 285° C., from 200° C. to 400° C., from 200° C. to 350° C., or from 200° C. to 300° C.

The isomerization reactors of the reverse isomerization unit 140 may be operated at an operating pressure of from 1,000 kilopascals (kPa) (10 bar) to 10,000 kPa (100 bar), such as from 1,000 kPa to 7,000 kPa, from 1,000 kPa to 4,000 kPa, from 1,000 kPa to 3,000 kPa, from 1,000 kPa to 2,000 kPa, from 2,000 kPa to 10,000 kPa, from 2,000 kPa to 7,000 kPa, from 2,000 kPa to 4,000 kPa, from 2,000 kPa to 3,000 kPa, from 3,000 kPa to 10,000 kPa, from 3,000 kPa to 7,000 kPa, or from 3,000 kPa to 4,000 kPa. In embodiments, the isoparaffin-rich stream 134 may comprise a high concentration of C5 isoparaffins, such as greater than or equal to 50 wt. %, or even greater than or equal to 75 wt. % C5 isoparaffins, and the pressure of the reverse isomerization unit 140 may be greater than or equal to 5,000 kPa (50 bar), such as from 5,000 kPa to 10,000 kPa. In embodiments, the isoparaffin-rich stream 134 may comprise a high concentration of isoparaffins having 6 or more carbon atoms, such as greater than or equal to 50 wt. %, or even greater than or equal to 75 wt. % C6+ isoparaffins, and the pressure of the reverse isomerization unit 140 may be greater than or equal to 4,000 kPa (40 bar), such as from 5,000 kPa to 10,000 kPa.

The isomerization reactor(s) of the reverse isomerization unit 140 may be operated at a hydrogen partial pressure of from 1,000 kPa (10 bar) to 10,000 kPa (100 bar), such as from 1,000 kPa to 8,000 kPa, from 1,000 kPa to 6,000 kPa, from 1,000 kPa to 4,000 kPa, from 1,000 kPa to 3,000 kPa, from 2,000 kPa to 10,000 kPa, from 2,000 kPa to 8,000 kPa, from 2,000 kPa to 6,000 kPa, from 2,000 kPa to 4,000 kPa, or from 4,000 kPa to 10,000 kPa. The isomerization reactor(s) of the reverse isomerization unit 140 may be operated at a liquid hourly space velocity (LHSV) of from 0.2 per hour ($h^{-1}$) to 20 $h^{-1}$, such as from 0.2 $h^{-1}$ to 10 $h^{-1}$, from 0.2 $h^{-1}$ to 5 $h^{-1}$, from 0.2 $h^{-1}$ to 3 $h^{-1}$, from 0.2 $h^{-1}$ to 2 $h^{-1}$, from 0.5 $h^{-1}$ to 20 $h^{-1}$, from 0.5 $h^{-1}$ to 10 $h^{-1}$, from 0.5 $h^{-1}$ to 5 $h^{-1}$, from 0.5 $h^{-1}$ to 3 $h^{-1}$, from 0.5 $h^{-1}$ to 2 $h^{-1}$, from 1 $h^{-1}$ to 20 $h^{-1}$, from 1 $h^{-1}$ to 10 $h^{-1}$, from 1 $h^{-1}$ to 5 $h^{-1}$, from 1 $h^{-1}$ to 3 $h^{-1}$, from 1 $h^{-1}$ to 2 $h^{-1}$, from 2 $h^{-1}$ to 20 $h^{-1}$, from 2 $h^{-1}$ to 10 $h^{-1}$, or from 2 $h^{-1}$ to 2 $h^{-1}$.

The isomerization reactor(s) of the reverse isomerization unit 140 may be operated at a mole ratio of hydrogen to hydrocarbon of from 0.01 to 20, such as from 0.01 to 15, from 0.01 to 10, from 0.01 to 5, from 0.01 to 1, from 0.02 to 20, from 0.02 to 15, from 0.02 to 10, from 0.02 to 5, from 0.02 to 1, from 0.1 to 20, from 0.1 to 15, from 0.1 to 10, from 1 to 20, from 1 to 15, or from 1 to 10. In embodiments, the isomerization reactors of the reverse isomerization unit 140 may be operated in the liquid phase. In these embodiments, the reaction conditions of the isomerization reactors (temperature, pressure, hydrogen partial pressure, LHSV) may be maintained at levels effective to maintain greater than or equal to 90 volume percent (vol %) of the feed to the isomerization reactors in the liquid phase, where the feed to the isomerization reactors comprises the isoparaffin-rich stream 134 and the hydrogen 142. In embodiments, the reaction conditions of the isomerization reactors (temperature, pressure, hydrogen partial pressure, LHSV) may be maintained at levels effective to maintain greater than or equal to 95 vol. % or greater than or equal to 98 vol. % of the feed to the isomerization reactors in the liquid phase, where the feed to the isomerization reactors comprises the isoparaffin-rich stream 134 and the hydrogen 142.

In embodiments, the reverse isomerization unit 140 may comprise at least two isomerization reactors arranged in series in a lead-lag configuration, where each of the isomerization reactors in series may be operated at a different operating temperature, which may maximize the approach to equilibrium between isoparaffins and normal paraffins. An upstream isomerization reactor may serve as a lead isomerization reactor and a downstream isomerization reactor may serve as the lag isomerization reactor. The operating temperature in the lead isomerization reactor may be greater than the operating temperature of the lag isomerization reactor. The greater temperature in the lead isomerization reactor may increase the rate of the isomerization reactor in a first stage of isomerization. The lesser operating temperature in the lag isomerization reactor may reduce the reaction rate to increase the approach to equilibrium.

Referring again to FIG. 1, the isomerate 144 may be passed out of the reverse isomerization unit 140. The isomerate 144 may comprise a mixture of normal paraffins and isoparaffins. In embodiments, a concentration of normal paraffins in the isomerate is greater than the concentration of normal paraffins in the isoparaffin-rich stream 134 passed to the reverse isomerization unit 140. In embodiments, the isomerate 144 may have an equilibrium composition of normal paraffins and isoparaffins. In embodiments, the isomerate 144 may comprise from 20 wt. % to 80 wt. % isoparaffins and from 20 wt. % to 80 wt. % normal paraffins based on the total weight of C4+ hydrocarbons in the isomerate 144. The isomerate 144 may further include excess hydrogen from the isomerization reactors and any C1-C3 hydrocarbons produced in the isomerization reactors through side reactors or passed through the isomerization reactors from the isoparaffin-rich stream 134. In embodiments, the isomerate 144 may be passed back to the paraffin separation system 130 for separation into the isoparaffin-rich streams 134 and the n-paraffin-rich streams 136.

Referring now to FIGS. 2-4, in embodiments, the isomerate 144 may be passed from the isomerization reactors of the reverse isomerization unit 140 to an isomerate separator 230 operable to remove light components from the isomerate 144 before passing the isoparaffins and normal paraffins to the paraffin separation system 130. In particular, the isomerate separator 230 may separate the isomerate 144 to produce at least an isomerate light gas stream 232, the C3-C4 isomerate effluent 234, and a C5+ isomerate effluent 236.

The isomerate light gas stream 232 may comprise hydrogen and C1-C2 hydrocarbons, such as but not limited to methane, ethane, ethylene, or combinations of these. The hydrogen may be excess hydrogen 142 not consumed in the isomerization reactors. The C1-C2 hydrocarbons may be produced in the isomerization reactors through side reactors or passed through the isomerization reactors from the isoparaffin-rich stream 134. The isomerate light gas stream 232 may comprise greater than or equal to 90%, greater than or equal to 95%, greater than or equal to 98%, or even greater than or equal to 99% of the hydrogen and C1-C2 hydrocarbons from the isomerate 144. The isomerate light gas stream 204 may be passed out of the system 100 to one or more downstream treatment units, such as hydrogen recovery and recycle, further separation, fuel gas, or other downstream process. In embodiments, any off gas comprising of methane and hydrogen can be sent to PSA for hydrogen recovery or directly used as fuel.

The C3-C4 isomerate effluent 234 may include hydrocarbons having 3-4 carbon atoms, such as but not limited to propane, propylene, n-butane, isobutane, butene, isobutene, or combinations of these. The C4-C4 hydrocarbons may be produced in the reverse isomerization unit 140 or passed from the isoparaffin-rich stream 134 through the reverse isomerization unit 140 without undergoing reaction. In embodiments, the C3-C4 isomerate effluent 234 may include greater than or equal to 75%, greater than or equal to 80%, greater than or equal to 85%, greater than or equal to 90%, greater than or equal to 95%, greater than or equal to 98%, or even greater than or equal to 99% of the C3-C4 hydrocarbons from the isomerate 144. The C3-C4 isomerate effluent 234 may be passed on to the paraffin separation system 130 or may be passed to the debutanizer system 250 for separation of the C3-C4 isomerate effluent 234 into the C3 product stream 252, the isobutane stream 254, and the n-butane stream 256. In some embodiments, the C2-C4 paraffins separated from the converted effluent 116 may be passed to a mixed feed steam cracker (not shown).

The C5+ isomerate effluent 236 may comprise the hydrocarbon constituents of the isomerate 144 having 5 or more carbon atoms. The C5+ isomerate effluent 236 may comprise greater than or equal to 90%, greater than or equal to 95%, greater than or equal to 98%, or even greater than or equal to 99% of the C5+ hydrocarbons from the isomerate 144. The C5+ isomerate effluent 236 may comprise isoparaffins and normal paraffins. The C5+ isomerate effluent 236 may comprise greater than 20 wt. %, greater than or equal to 30 wt. %, greater than or equal to 40 wt. %, or even greater than or equal to 50 wt. % n-paraffins based on the total weight of the C5+ isomerate effluent 236. In embodiments, the C5+ isomerate effluent 236 may comprise from 20 wt. % to 80 wt. %, from 20 wt. % to 75 wt. %, from 20 wt. % to 70 wt. %, from 20 wt. % to 60 wt. %, from 30 wt. % to 80 wt. %, from 30 wt. % to 75 wt. %, from 30 wt. % to 70 wt. %, from 30 wt. % to 60 wt. %, from 40 wt. % to 80 wt. %, from 40 wt. % to 75 wt. %, from 40 wt. % to 70 wt. %, from 40 wt. % to 60 wt. %, from 45 wt. % to 80 wt. %, from 45 wt. % to 75 wt. %, from 45 wt. % to 70 wt. %, from 45 wt. % to 60 wt. %, from 50 wt. % to 80 wt. %, from 50 wt. % to 75 wt. %, from 50 wt. % to 70 wt. %, from 50 wt. % to 60 wt. %, or from 60 wt. % to 20 wt. % n-paraffins based on the total weight of the C5+ isomerate effluent 236. The balance of the C5+ isomerate effluent 236 may generally comprise isoparaffins, but may also include small concentrations of hydrogen and hydrocarbons having less than 5 carbon atoms that are not 100% separated out by the isomerate separator 230.

Referring again to FIGS. 2-4, the C5+ isomerate effluent 236 may be passed to the paraffin separation system 130 for separation of the C5+ isomerate effluent 236 into the one or more isoparaffin-rich streams 134 and the one or more n-paraffin-rich streams 136. The C5+ isomerate effluent 236 may be passed directly to the paraffin separation system 130 or may be combined with the light naphtha 212 upstream of the paraffin separation system 130. In embodiments, a C5+ slip stream 237 may be divided off of the C5+ isomerate effluent 236 and passed directly to the steam cracker 150 to reduce build-up of isoparaffins in the reverse isomerization system 120.

Referring again to FIG. 1, the system 100 may include the steam cracker 150 disposed downstream of the reverse isomerization system 120. Various streams comprising n-paraffins may be passed from the naphthene conversion unit 110, the reverse isomerization system 120, the debutanizer system 250, or combinations of these to the steam cracker 150. Referring to FIGS. 2-4, in embodiments, one or more of the C5+ slip stream 209, the heavy naphtha 214, the C5+ slip stream 237 from the isomerate separator 230, any of the n-paraffin-rich streams, the n-butane stream 256, or combinations of these streams may be passed to the steam cracker 150. The n-paraffin-rich streams include, but are not limited to, the C5 n-paraffin stream 174 (FIG. 2), the C6 n-paraffin stream 176 (FIG. 2), the drag stream 178 (FIG. 2), the C5 n-paraffin stream 184 (FIG. 3), the C6 n-paraffin stream 194 (FIG. 3), the drag stream 196 (FIG. 3), the n-paraffin-rich stream 304 (FIG. 4), or combinations of these n-paraffin-rich streams.

The steam cracker 150 may be operable to contact the slip streams, heavy naphtha, n-paraffin-rich streams, or combinations of these stream with steam at temperatures sufficient to cause the hydrocarbons in these streams to undergo thermal cracking to produce one or more cracking effluents 152. The cracking effluent 152 may comprise one or more products, such as but not limited to ethylene or other olefins. The cracking effluent 152 may be passed to a cracking effluent separation system (not shown) to separate the cracking effluent 152 to produce ethylene.

The systems 100 and methods of the present disclosure are configured to convert naphthenes to paraffins and to isomerize isoparaffins to normal paraffins for purposes of increasing the quantity or proportion of normal paraffins to the steam cracker 150. Increasing the proportion of normal paraffins to the steam cracker 150 may increase the selectivity of the steam cracking process towards greater yield of ethylene over other olefins such as propylene and mixed butenes. Steam cracking normal paraffins produce a greater yield of ethylene compared to steam cracking isoparaffins. Table 1 provide the yields of ethylene, propylene, and mixed butenes resulting from steam cracking of a normal butane feed, an isobutane feed, a normal pentane feed, and an isopentane feed. As shown in Table 1, the normal butane feed produces a greater yield of ethylene and lower yields of propylene and mixed butenes compared to the isobutane feed. Likewise, the normal pentane feed produces a greater yield of ethylene and lower yields of propylene and mixed butenes compared to the isopentane feed. Steam cracking normal paraffins can produce nearly twice as much ethylene compared to steam cracking isoparaffins. Thus, increasing the proportion of normal paraffins to the steam cracker 150 can increase the yield of ethylene produced in the steam cracker 150.

TABLE 1

Yields of olefin products from steam cracking of normal
paraffin feeds and isoparaffin feeds

| Feed Stream | Normal butane | Iso-Butane | Normal Pentane | Iso-Pentane |
|---|---|---|---|---|
| Ethylene yield (wt. %) | 40.2 | 13.2 | 41.3 | 21.4 |
| Propylene yield (wt. %) | 15.3 | 21.9 | 15.4 | 17.0 |
| Mixed butenes yield (wt. %) | 1.7 | 17.4 | 2.5 | 12.5 |

Figure 5:
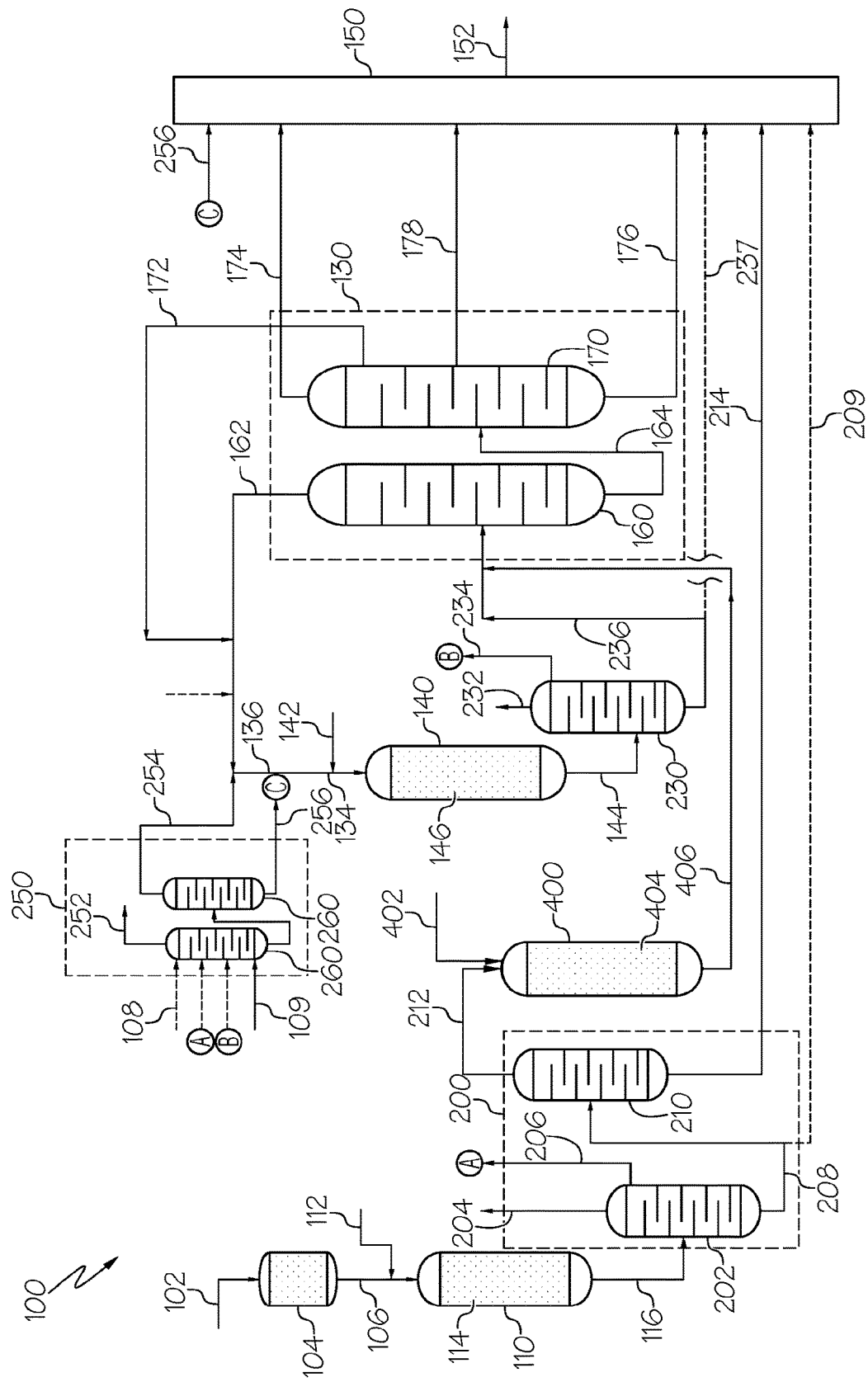
FIG. 5 schematically depicts a generalized flow diagram of another system for upgrading a naphtha feed, including desulfurizing the naphtha feed, according to one or more embodiments shown and described in this disclosure.

Referring now to FIG. 5, in embodiments, the system 100 may further comprise a hydrogenation unit 400 disposed between the naphthene conversion unit 110 and the reverse isomerization system 120. In embodiments, the hydrogenation unit 400 may be disposed between the naphtha separation unit 210 and the paraffin separation system 130. As previously discussed, in embodiments, the incoming naphtha feed 104 may contain benzene or other aromatic compounds having aromatic ring structures. At least a portion of the benzene and other aromatic compounds can be hydrogenated in the naphthene conversion unit 110. However, if the concentrations of benzene and other aromatic compounds in the naphtha feed 104 is too great, incomplete hydrogenation may occur and benzene and other aromatic compounds can pass through the naphthene conversion unit 110. Depending on the cut point temperature of the naphtha separation unit 210, benzene or other aromatic compounds may end up in the light naphtha 212 passed downstream to the reverse isomerization system 120. The presence of aromatic compounds can reduce the yield of ethylene from the steam cracker 150.

The hydrogenation unit 400 may hydrogenate benzene and other aromatic compounds in the light naphtha 212 to produce additional paraffins, which may be n-paraffins, isoparaffins, cycloalkanes, or combinations of these. The hydrogenation unit 400 may contact the light naphtha 212 with hydrogen 402 in the presence of a hydrogenation catalyst 404 at conditions that cause at least a portion of the aromatic compounds in the light naphtha 212 to undergo hydrogenation to produce a hydrogenated effluent 406 having a concentration of aromatic compounds less than a concentration of aromatic compounds in the light naphtha 212. The hydrogenation catalyst may comprise one or more active phase metals, such as but not limited to nickel, molybdenum, platinum, palladium, or combinations of these, the active phase metals may be supported on an amorphous or crystalline support comprising alumina, silica, or combinations of these.

The hydrogenated effluent 406 may comprise the C5 and C6 paraffin compounds from the light naphtha 212, any additional paraffins or cycloparaffins produced through hydrogenation of aromatic compounds, and any aromatic compounds passing through the hydrogenation unit 400. In embodiments, the hydrogenated effluent 406 may have less than 5 wt. %, less than or equal to 3 wt. %, less than or equal to 1 wt. %, less than or equal to 0.5 wt. %, or even less than or equal to 0.1 wt. % aromatic compounds based on the total weight of the hydrogenated effluent 406. The hydrogenated effluent 406 may be passed along to the paraffin separation system 130.

Referring again to FIG. 1, the system 100 previously discussed herein can be used in a process for upgrading a hydrocarbon feed. The process may include passing the hydrocarbon feed, such as but not limited to the naphtha feed 104, to the naphthene conversion unit 110, where the hydrocarbon feed comprises naphthenes. The process can further include contacting the hydrocarbon feed with hydrogen 112 in the presence of the ring opening catalyst 114 in the naphthene conversion unit 110, where the contacting causes at least a portion of the naphthenes in the hydrocarbon feed to react to produce the converted effluent 116 comprising at least isoparaffins and normal paraffins. The process may further include separating at least a portion of the converted effluent 116 in a paraffin separation system 130 to produce at least one isoparaffin-rich stream 134 and at least one n-paraffin-rich stream 136, passing the at least one isoparaffin-rich stream 134 to the reverse isomerization unit 140, and contacting the at least one isoparaffin-rich stream 134 with hydrogen 142 in the presence of the isomerization catalyst 146 in the reverse isomerization unit 140, where the contacting in the reverse isomerization unit 140 may cause at least a portion of the isoparaffins in the at least one isoparaffin-rich stream 134 to undergo isomerization to produce the isomerate 144 comprising a mixture of normal paraffins and isoparaffins. In embodiments, the isomerate 144 may comprise an equilibrium mixture of normal paraffins and isoparaffins. The process may further include passing at least a portion of the isomerate 144 to the paraffin separation system 130 that separates the portion of the isomerate 144 to produce the at least one isoparaffin-rich stream 134 and the at least one n-paraffin-rich stream 136 and passing the at least one n-paraffin-rich stream 136 to the steam cracker 150 to produce the cracker effluent 152, which comprises at least one product. The naphthene conversion unit 110, paraffin separation system 130, reverse-isomerization unit 140, and steam cracker 150 may have any of the features, catalysts, or operating conditions previously described in the present disclosure for these unit operations. The various streams may have any of the properties or compositions previously described in the present disclosure for each of the various streams.

In embodiments, the hydrocarbon feed may comprise the naphtha feed 102 comprising a straight run naphtha, a hydrotreated naphtha, or combinations of these. The naphtha feed 102 may have any of the properties or compositions previously discussed herein for the naphtha feed 102. In embodiments, the hydrocarbon feed may further comprise the butane-containing stream 108. The butane-containing stream 108 may have any of the properties or compositions previously discussed for the butane-containing stream 108. The hydrocarbon feed may include any other feed streams previous discussed in the present disclosure. The hydrocarbon feed may have an average carbon number of from 4 to 12. In embodiments, the hydrocarbon feed may comprise from 40 wt. % to 60 wt. % naphthenes based on the total weight of the hydrocarbon feed. In embodiments, the hydrocarbon feed may have a molar ratio of iso-paraffins to normal paraffins of from 0.5 to 4, or from 2 to 4. In embodiments, the hydrocarbon feed may have a boiling point temperature range of from −5° C. to 220° C., such as from 36° C. to 220° C. The hydrocarbon feed may have any other property previously discussed.

The at least one product in the cracker effluent may comprise ethylene. The processes of the present disclosure may produce a greater yield of ethylene compared to steam cracking the hydrocarbon feed directly without converting naphthenes to paraffins and without isomerizing isoparaffins to normal paraffins.

The processes may further include passing the butane-containing stream 108 to the paraffin separation system 130 that separates the butane-containing stream 108 into the at least one isoparaffin-rich stream 134 and the at least one n-paraffin-rich stream 136, where the at least one isoparaffin-rich stream 134 comprises isobutane from the butane-containing stream 108 and the at least one n-paraffin-rich stream 136 comprises normal butane from the butane-containing stream 108.

Referring still to FIG. 1, in embodiments, the naphthene conversion unit 110 may comprise one or more fixed bed reactors, ebullated bed reactors, moving bed reactors, or combinations of these. In embodiments, the naphthene conversion unit 110 may be a vapor phase reaction system or a two-phase reaction system. The processes may comprise contacting the hydrocarbon feed with the hydrogen 112 in the presence of the ring opening catalyst 114 in the naphthene conversion unit 110 at any of the reaction conditions previously discussed, such as but not limited to: a naphthene conversion temperature of from 150° C. to 400° C.; a naphthene conversion pressure of from 1000 kPa to 10,000 kPa (10 bars to 100 bars); a hydrogen partial pressure of from 1000 kPa to 6000 kPa; a liquid hourly space velocity of from 0.2 hour-1 to 20 hour-1; or combinations of these operating conditions. In embodiments, the converted effluent comprises at least 75% paraffins, at least 90% paraffins, or at least 98% paraffins. In embodiments, a conversion of naphthenes in the naphthene conversion unit may be greater than or equal to 95 wt. % based on the total weight of naphthenes in the hydrocarbon feed.

The ring opening catalyst may have any of the compositions or characteristics previously discussed in the present disclosure for the ring opening catalyst. In embodiments, the ring opening catalyst may comprise one or more transition metals from groups 8-10 of the IUPAC periodic table supported on a catalyst support comprising alumina, silica, titania, or combinations of these. In embodiments, the one or more transition metals may be selected from the group consisting of Ir, Pt, Pd, Rh, Ru, and combinations of these metals. In embodiments, the catalyst support may be non-acidic or mildly acidic.

Referring again to FIG. 1, in embodiments, the reverse isomerization unit 140 may comprise one or more fixed bed reactors, ebullated bed reactors, moving bed reactors, or combinations of these. In embodiments, the reverse isomerization unit 140 may be a vapor phase reaction system or a two-phase reaction system. The processes may comprise contacting the at least one isoparaffin-rich stream 134 with hydrogen 142 in the presence of an isomerization catalyst 146 in the reverse isomerization unit 140 at any of the reaction conditions previously discussed, such as but not limited to: a reverse isomerization temperature of from 20° C. to 400° C.; a reverse isomerization pressure of from 1000 kPa to 10,000 kPa (10 bars to 100 bars); a liquid hourly space velocity of from 0.2 hour-1 to 20 hour-1; a mole ratio of hydrogen to hydrocarbons of from 0.01 to 20; or combinations of these operating conditions.

The isomerization catalyst 146 may have any of the compositions or characteristics previously discussed in the present disclosure for the isomerization catalyst. In embodiments, the isomerization catalyst in the reverse isomerization unit 140 may comprise one or more noble metals supported on a catalyst support. In embodiments, the one or more noble metals may be selected from the group consisting of iridium (Ir), platinum (Pt), palladium (Pd), rhodium (Rh), ruthenium (Ru), and combinations of these noble metals. In embodiments, the catalyst support may comprise chlorinated alumina, sulfonated zirconium, zeolites, or combinations of these catalyst supports.

Referring again to FIG. 2, in embodiments, the paraffin separation system 130 may comprise a two-stage fractionation system comprising the first fractionation column 160 and the second fractionation column 170. The processes may further include passing at least a portion of the isomerate 144 and at least a portion of the converted effluent 116 to the first fractionation column 160 that separates the portion of the isomerate 144 and the portion of the converted effluent 116 to produce the C5 isoparaffin stream 162 and the bottom stream 164; passing the bottom stream 164 to the second fractionation column 172 that separates the bottoms stream 164 to produce at least the C6 isoparaffin stream 172, the C5 n-paraffin stream 174, and the C6 n-paraffin stream 176; passing the C5 isoparaffin stream 162 and the C6 isoparaffin stream 172 to the reverse isomerization unit 140, where the isoparaffin-rich stream 134 comprises the C5 isoparaffin stream 162 and the C6 isoparaffin stream 172; and passing the C5 n-paraffin stream 174 and the C6 n-paraffin stream 176 to the steam cracker 150, where the n-paraffin-rich stream 136 comprises the C5 n-paraffin stream 174 and the C6 n-paraffin stream 176.

Referring again to FIG. 3, in embodiments, the paraffin separation unit 130 may comprise a first divided-wall fractionation column 180 and a second divided-wall fractionation column 190 downstream of the first divided-wall fractionation column 180. In embodiments, the processes may include passing at least a portion of the isomerate 144 and at least a portion of the converted effluent 116 to the first divided-wall fractionation column 180 that separates the portion of the isomerate 144 and the portion of the converted effluent 116 to produce the C5 isoparaffin stream 182, the C5 n-paraffin stream 184, and the C6+ bottom stream 186; passing the C6+ bottom stream 186 to the second divided-wall fractionation column 190 that separates the C6+ bottoms stream 186 to produce at least the C6 isoparaffin stream 192 and the C6 n-paraffin stream 194; passing the C5 isoparaffin stream 182 and the C6 isoparaffin stream 192 to the reverse isomerization unit 140; and passing the C5 n-paraffin stream 184 and the C6 n-paraffin stream 194 to the steam cracker 150.

Referring again to FIG. 4, in embodiments, the paraffin separation system 130 may comprise the adsorption separation unit 300. In embodiments, the processes may include passing at least a portion of the isomerate 144 and at least a portion of the converted effluent 116 to the adsorption separation unit 300 that separates the portion of the isomerate 144 and the portion of the converted effluent 116 to produce the isoparaffin-rich stream 134 and the n-paraffin-rich stream 136, passing the isoparaffin-rich stream 134 to the reverse isomerization unit 140, and passing the n-paraffin-rich stream 136 to the steam cracker 150.

Referring again to FIG. 2, in embodiments, the processes may further include passing the converted effluent 116 to a converted effluent separation system 200 that separates the converted effluent 116 to produce at least the light naphtha 212 and the heavy naphtha 214, passing the heavy naphtha 214 to the steam cracking unit 250, and passing the light naphtha 212 to the paraffin separation system 130. The converted effluent separation system 200 may also separate the converted effluent 116 to further produce the light gas stream 204, the C3-C4 effluent 206, or both. The processes may include passing the C3-C4 effluent 206 to the debutanizer system 250 for separating the butane-containing stream 108.

Referring again to FIG. 5, in embodiments, the processes may include, when the concentration of aromatic compounds in the light naphtha 212 is greater than or equal to 5 wt. % based on the total weight of the light naphtha 212, passing the light naphtha 212 to the hydrogenation unit 400 disposed downstream of the converted effluent separation system 200 and upstream of the paraffin separation system 130. The processes may further include contacting the light naphtha 212 with a hydrogen 402 in the presence of a hydrogenation catalyst 404 in the hydrogenation unit 400, where the contacting causes at least a portion of the aromatic compounds in the light naphtha 212 to undergo hydrogenation to produce a hydrogenated effluent 406 having a reduced concentration of aromatic compounds compared to the light naphtha 212. The processes may further include passing the hydrogenated effluent 406 to the paraffin separation system 130.

Referring again to FIG. 2, in embodiments, the processes may further include passing the butane-containing stream 108 to the dubutanizer system 250 that separates the butane-containing stream 108 into the isobutane stream 254 and the n-butane stream 256, passing the isobutane stream 254 to the reverse isomerization unit 140, and passing the n-butane stream to the steam cracker. In embodiments, the processes may further include passing the isomerate 144 to the isomerate separator 230 that separates the isomerate 140 to produce at least the isomerate light gas stream 232, the C3-C4 isomerate effluent 234, and the C5+ isomerate effluent 236; and passing the C5+ isomerate effluent 236 to the paraffin separation system 130. In embodiments, the processes may include passing the C3-C4 isomerate effluent 234 to the debutanizer system 250 along with the butane-containing stream 108.

Referring again to FIG. 2, in embodiments, the processes may further include conditioning at least a portion of the hydrocarbon feed, such as but not limited to the naphtha feed 102, in one or more guard beds 104 prior to passing the hydrocarbon feed to the naphthene conversion unit 110. The guard bed 104 may comprise a desulfurization catalyst, and conditioning the hydrocarbon feed in the one or more guard beds 104 may comprise contacting the hydrocarbon feed with the desulfurization catalyst, where the contacting the hydrocarbon feed with the desulfurization catalyst reduces a concentration of sulfur in the hydrocarbon feed to produce a conditioned hydrocarbon feed.

One or more aspects of the present disclosure are described herein. A first aspect of the present disclosure may include a process for upgrading a hydrocarbon feed, the process comprising passing the hydrocarbon feed to a naphthene conversion unit, where the hydrocarbon feed may comprise naphthenes. The process may further comprise contacting the hydrocarbon feed with hydrogen in the presence of a ring opening catalyst in the naphthene conversion unit, where the contacting may cause at least a portion of the naphthenes in the hydrocarbon feed to react to produce a converted effluent comprising at least isoparaffins and normal paraffins. The process may further include passing at least a portion of the converted effluent to a paraffin separation system that may separate the at least a portion of the converted effluent to produce least one isoparaffin-rich stream and at least one n-paraffin-rich stream. The process may further include passing the at least one isoparaffin-rich stream to a reverse isomerization unit and contacting the at least one isoparaffin-rich stream with hydrogen in the presence of an isomerization catalyst in the reverse isomerization unit, where the contacting in the reverse isomerization unit may cause at least a portion of the isoparaffins in the at least one isoparaffin-rich stream to undergo isomerization to produce an isomerate comprising a mixture of normal paraffins and isoparaffins. The process may further include passing at least a portion of the isomerate to the paraffin separation system that may separate the at least a portion of the isomerate to produce the at least one isoparaffin-rich stream and the at least one n-paraffin-rich stream, and passing the at least one n-paraffin-rich stream to a steam cracker to produce a cracker effluent comprising at least one product.

A second aspect of the present disclosure may include the first aspect, where the hydrocarbon feed may comprise a naphtha feed comprising a straight run naphtha, a hydrotreated naphtha, or combinations of these.

A third aspect of the present disclosure may include the second aspect, where the hydrocarbon feed may further comprises a butane-containing stream.

A fourth aspect of the present disclosure may include any one of the first through third aspects, further comprising passing a butane-containing stream to the paraffin separation system that separates the butane-containing stream into the at least one isoparaffin-rich stream and the at least one n-paraffin-rich stream. The at least one isoparaffin-rich stream may comprise isobutane from the butane-containing stream, and the at least one n-paraffin-rich stream may comprise normal butane from the butane-containing stream.

A fifth aspect of the present disclosure may include any one of the first through fourth aspects, where the hydrocarbon feed may comprise an average carbon number of from 4 to 12.

A sixth aspect of the present disclosure may include any one of the first through fifth aspects, where the hydrocarbon feed may comprise from 40 wt. % to 60 wt. % naphthenes based on the total weight of the hydrocarbon feed.

A seventh aspect of the present disclosure may include any one of the first through sixth aspects, where the hydrocarbon feed may have a molar ratio of iso-paraffins to normal paraffins of from 1:2 to 4:1, such as from 1:2 to 3:1, from 1:2 to 2:1, from 2:1 to 4:1, or from 2:1 to 3:1.

A eighth aspect of the present disclosure may include any one of the first through seventh aspects, where the hydrocarbon feed may have a boiling point temperature range of from −5° C. to 220° C., such as from 36° C. to 220° C.

A ninth aspect of the present disclosure may include any one of the first through eighth aspects, where the at least one product may comprise ethylene.

A tenth aspect of the present disclosure may include any one of the first through ninth aspects, where the naphthene conversion unit may comprise one or more fixed bed reactors, ebullated bed reactors, moving bed reactors, or combinations of these.

An eleventh aspect of the present disclosure may include any one of the first through tenth aspects, comprising contacting the hydrocarbon feed with the hydrogen in the presence of the ring opening catalyst in the naphthene conversion unit at one or more of the following reaction conditions: a naphthene conversion temperature of from 150° C. to 400° C.; a naphthene conversion pressure of from 1000 kPa to 10,000 kPa (10 bars to 100 bars); a hydrogen partial pressure of from 1000 kPa to 6000 kPa; a liquid hourly space velocity of from 0.2 hour$^{-1}$ to 20 hour$^{-1}$; or combinations of these operating conditions.

A twelfth aspect of the present disclosure may include any one of the first through eleventh aspects, where the ring opening catalyst may comprise one or more transition metals from groups 8-10 of the IUPAC periodic table supported on a catalyst support comprising alumina, silica, titania, or combinations of these.

A thirteenth aspect of the present disclosure may include the twelfth aspect, where the one or more transition metals may be selected from the group consisting of Ir, Pt, Pd, Rh, Ru, and combinations of these metals.

A fourteenth aspect of the present disclosure may include either one of the twelfth or thirteenth aspects, where the catalyst support may be non-acidic or mildly acidic.

A fifteenth aspect of the present disclosure may include any one of the first through fourteenth aspects, where the converted effluent may comprise at least 75% paraffins, at least 90% paraffins, or at least 98% paraffins.

A sixteenth aspect of the present disclosure may include any one of the first through fifteenth aspects, where a conversion of naphthenes in the naphthene conversion unit may be greater than or equal to 95 wt. % based on the total weight of naphthenes in the hydrocarbon feed.

A seventeenth aspect of the present disclosure may include any one of the first through sixteenth aspects, comprising contacting the at least one isoparaffin-rich stream with hydrogen in the presence of an isomerization catalyst in the reverse isomerization unit at one or more of the following reaction conditions: a reverse isomerization temperature of from 20° C. to 400° C.; a reverse isomerization pressure of from 1000 kPa to 10,000 kPa (10 bars to 100 bars); a liquid hourly space velocity of from 0.2 hour$^{-1}$ to 20 hour$^{-1}$; a mole ratio of hydrogen to hydrocarbons of from 0.01 to 20; or combinations of these operating conditions.

An eighteenth aspect of the present disclosure may include any one of the first through seventeenth aspects, where the isomerization catalyst in the reverse isomerization unit may comprise one or more noble metals supported on a catalyst support.

A nineteenth aspect of the present disclosure may include the eighteenth aspect, where the one or more noble metals may be selected from the group consisting of iridium (Ir), platinum (Pt), palladium (Pd), rhodium (Rh), ruthenium (Ru), and combinations of these noble metals.

A twentieth aspect of the present disclosure may include either one of the eighteenth or nineteenth aspects, where the catalyst support may comprise chlorinated alumina, sulfonated zirconium, zeolites, or combinations of these catalyst supports.

A twenty-first aspect of the present disclosure may include any one of the first through twentieth aspects, where the isomerate may be an equilibrium mixture of normal paraffins and isoparaffins.

A twenty-second aspect of the present disclosure may include any one of the first through twenty-first aspects, where the paraffin separation system may comprise a two-stage fractionation system comprising a first fractionation column and a second fractionation column.

A twenty-third aspect of the present disclosure may include the twenty-second aspect, comprising: passing the at least a portion of the isomerate and the at least a portion of the converted effluent to the first fractionation column that separates the portion of the isomerate and the portion of the converted effluent to produce a C5 isoparaffin stream and a bottom stream; passing the bottom stream to the second fractionation column that separates the bottoms stream to produce at least a C6 isoparaffin stream, a C5 n-paraffin stream, and a C6 n-paraffin stream; passing the C5 isoparaffin stream and the C6 isoparaffin stream to the reverse isomerization unit, where the isoparaffin-rich stream may comprise the C5 isoparaffin stream and the C6 isoparaffin stream; and passing the C5 n-paraffin stream and the C6 n-paraffin stream to the steam cracker, where the n-paraffin-rich stream may comprise the C5 n-paraffin stream and the C6 n-paraffin stream.

A twenty-fourth aspect of the present disclosure may include any one of the first through twenty-third aspects, where the paraffin separation system may comprise a first divided-wall fractionation column and a second divided-wall fractionation column downstream of the first divided-wall fractionation column.

A twenty-fifth aspect of the present disclosure may include the twenty-fourth aspect, comprising: passing the at least a portion of the isomerate and the at least a portion of the converted effluent to the first divided-wall fractionation column that separates the portion of the isomerate and the portion of the converted effluent to produce a C5 isoparaffin stream, a C5 n-paraffin stream, and a C6+ bottom stream; passing the C6+ bottom stream to the second divided-wall fractionation column that separates the C6+ bottoms stream to produce at least a C6 isoparaffin stream, and a C6 n-paraffin stream; passing the C5 isoparaffin stream and the C6 isoparaffin stream to the reverse isomerization unit; and passing the C5 n-paraffin stream and the C6 n-paraffin stream to the steam cracker.

A twenty-sixth aspect of the present disclosure may include any one of the first through twenty-fifth aspects, where the paraffin separation system may comprise an adsorption separation unit.

A twenty-seventh aspect of the present disclosure may include the twenty-sixth aspect, comprising: passing the at least a portion of the isomerate and the at least a portion of the converted effluent to the adsorption separation unit that separates the portion of the isomerate and the portion of the converted effluent to produce the isoparaffin-rich stream and the n-paraffin-rich stream; passing the isoparaffin-rich stream to the reverse isomerization unit; and passing the n-paraffin-rich stream to the steam cracker.

A twenty-eighth aspect of the present disclosure may include any one of the first through twenty-seventh aspects, further comprising: passing the converted effluent to a converted effluent separation system that separates the converted effluent to produce at least a light naphtha and a heavy naphtha; passing the heavy naphtha to the steam cracking unit; and passing the light naphtha to the paraffin separation system.

A twenty-ninth aspect of the present disclosure may include the twenty-eighth aspect, further comprising, when a concentration of aromatic compounds in the light naphtha is greater than or equal to 5 weight percent based on the total weight of the light naphtha, passing the light naphtha to a hydrogenation unit disposed downstream of the converted effluent separation system and upstream of the paraffin separation system; contacting the light naphtha with a hydrogen in the presence of a hydrogenation catalyst in the hydrogenation unit, where the contacting may cause at least a portion of the aromatic compounds in the light naphtha to undergo hydrogenation to produce a hydrogenated effluent having a reduced concentration of aromatic compounds; and passing the hydrogenated effluent to the paraffin separation system.

A thirtieth aspect of the present disclosure may include any one of the first through twenty-ninth aspects, further comprising: passing a butane-containing stream to a dubutanizer system that separates the butane-containing stream into an isobutane stream and an n-butane stream; passing the isobutane stream to the reverse isomerization unit; and passing the n-butane stream to the steam cracker.

A thirty-first aspect of the present disclosure may include any one of the first through thirtieth aspects, further comprising: passing the isomerate to an isomerate separator that separates the isomerate to produce at least an isomerate light gas stream, a C3-C4 isomerate effluent, and a C5+ isomerate effluent; and passing the C5+ isomerate effluent to the paraffin separation system.

A thirty-second aspect of the present disclosure may include any one of the first through thirty-first aspects, further comprising conditioning the hydrocarbon feed in one or more guard beds prior to passing the hydrocarbon feed to the naphthene conversion unit.

A thirty-third aspect of the present disclosure may include the thirty-second aspect, where the guard bed comprises a desulfurization catalyst, and conditioning the hydrocarbon feed in the one or more guard beds comprises contacting the hydrocarbon feed with the desulfurization catalyst, where the contacting the hydrocarbon feed with the desulfurization catalyst reduces a concentration of sulfur in the hydrocarbon feed to produce a conditioned hydrocarbon feed.

A thirty-fourth aspect of the present disclosure may include any one of the first through thirty-third aspects, where the naphthene conversion unit may be a vapor phase reaction system or a two-phase reaction system.

A thirty-fifth aspect of the present disclosure may include anyone of the first through thirty-fourth aspects, where the reverse isomerization unit may operate in a liquid phase, a vapor phase, or both.

A thirty-sixth aspect of the present disclosure may be directed to a system comprising: a naphthene conversion unit comprising a ring opening catalyst, the naphthene conversion unit operable to convert naphthenes from a naphtha feed to produce a converted effluent comprising a mixture of isoparaffins and n-paraffins; a reverse isomerization unit disposed downstream of the naphthene conversion unit, the reverse isomerization unit comprising an isomerization catalyst and operable to convert isoparaffins from at least one isoparaffin rich stream to n-paraffins to produce an isomerate comprising a concentration of n-paraffins greater than a concentration of n-paraffins in the at least one isoparaffin-rich stream; a paraffin separation system operable to separate at least a portion of the converted effluent and at least a portion of the isomerate to produce the at least one isoparaffin-rich stream and at least one n-paraffin-rich stream; and a steam cracker disposed downstream of the paraffin separation system and operable to steam crack the at least one n-paraffin-rich stream to produce a cracker effluent comprising at least ethylene.

It is noted that one or more of the following claims utilize the term "where" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that any two quantitative values assigned to a property may constitute a range of that property, and all combinations of ranges formed from all stated quantitative values of a given property are contemplated in this disclosure.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

What is claimed is:

1. A process for upgrading a hydrocarbon feed, the process comprising:
   passing the hydrocarbon feed to a naphthene conversion unit, where the hydrocarbon feed comprises naphthenes;
   contacting the hydrocarbon feed with hydrogen in the presence of a ring opening catalyst in the naphthene conversion unit, where the contacting causes at least a portion of the naphthenes in the hydrocarbon feed to react to produce a converted effluent comprising at least isoparaffins and normal paraffins;
   passing at least a portion of the converted effluent to a paraffin separation system that separates the at least a portion of the converted effluent to produce at least one isoparaffin-rich stream and at least one n-paraffin-rich stream;
   passing a butane-containing stream to the paraffin separation system that separates the butane-containing stream into the at least one isoparaffin-rich stream and the at least one n-paraffin-rich stream, wherein the at least one isoparaffin-rich stream comprises isobutane from the butane-containing stream, and the at least one n-paraffin-rich stream may comprise normal butane from the butane-containing stream;
   passing the at least one n-paraffin-rich stream to a steam cracker to produce a cracker effluent comprising at least one product.

2. The process of claim 1, further comprising passing the at least one isoparaffin-rich stream to a reverse isomerization unit.

3. The process of claim 2, wherein the reverse isomerization unit operates in a liquid phase, a vapor phase, or both.

4. The process of claim 2, further comprising contacting the at least one isoparaffin-rich stream with hydrogen in the presence of an isomerization catalyst in the reverse isomerization unit, where the contacting in the reverse isomerization unit causes at least a portion of the isoparaffins in the at least one isoparaffin-rich stream to undergo isomerization to produce an isomerate comprising a mixture of normal paraffins and isoparaffins.

5. The process of claim 4, further comprising passing at least a portion of the isomerate to the paraffin separation system that separates the at least a portion of the isomerate to produce the at least one isoparaffin-rich stream and the at least one n-paraffin-rich stream.

6. The process of claim 4, further comprising:
   passing the isomerate to an isomerate separator that separates the isomerate to produce at least an isomerate light gas stream, a C3-C4 isomerate effluent, and a C5+ isomerate effluent; and
   passing the C5+ isomerate effluent to the paraffin separation system.

7. The process of claim 1, wherein the naphthene conversion unit comprises one or more fixed bed reactors, ebullated bed reactors, moving bed reactors, or combinations thereof.

8. The process of claim 1, wherein the ring opening catalyst comprises one or more transition metals from groups 8-10 of the IUPAC periodic table supported on a catalyst support comprising alumina, silica, titania, or combinations thereof.

9. The process of claim 8, where the one or more transition metals may be selected from the group consisting of Ir, Pt, Pd, Rh, Ru, and combinations of these metals.

10. The process of claim 8, wherein the catalyst support may be non-acidic or mildly acidic.

11. The process of claim 1, wherein a conversion of naphthenes in the naphthene conversion unit is greater than or equal to 95 wt. % based on a total weight of naphthenes in the hydrocarbon feed.

12. The process of claim 1, further comprising conditioning the hydrocarbon feed in one or more guard beds prior to passing the hydrocarbon feed to the naphthene conversion unit.

13. The process of claim 12, wherein:
the guard bed comprises a desulfurization catalyst; and
conditioning the hydrocarbon feed in the one or more guard beds comprises contacting the hydrocarbon feed with the desulfurization catalyst, wherein the contacting the hydrocarbon feed with the desulfurization catalyst reduces a concentration of sulfur in the hydrocarbon feed to produce a conditioned hydrocarbon feed.

14. The process of claim 1, wherein the naphthene conversion unit is a vapor phase reaction system or a two-phase reaction system.

15. The process of claim 1, where the hydrocarbon feed comprises a naphtha feed comprising a straight run naphtha, a hydrotreated naphtha, or combinations of these.

16. The process of claim 1, where the hydrocarbon feed comprises an average carbon number of from 4 to 12, a boiling point temperature range of from −5° C. to 220° C., or both.

17. The process of claim 1, where the hydrocarbon feed comprises from 40 wt. % to 60 wt. % naphthenes based on a total weight of the hydrocarbon feed, a molar ratio of iso-paraffins to normal paraffins of from 1:2 to 4:1, or both.

18. The process of claim 1, comprising contacting the hydrocarbon feed with the hydrogen in the presence of the ring opening catalyst in the naphthene conversion unit at one or more of the following reaction conditions:

a naphthene conversion temperature of from 150° C. to 400° C.;

a naphthene conversion pressure of from 1000 kPa to 10,000 kPa (10 bars to 100 bars);

a hydrogen partial pressure of from 1000 kPa to 6000 kPa;

a liquid hourly space velocity of from 0.2 hour$^{-1}$ to 20 hour$^{-1}$; or combinations of these operating conditions.

19. The process of claim 1, where the converted effluent comprises at least 75% paraffins, wherein the paraffins include normal paraffins, isoparaffins, or combinations thereof.

20. The process of claim 1, further comprising:

passing the converted effluent to a converted effluent separation system that separates the converted effluent to produce at least a light naphtha and a heavy naphtha;

passing the heavy naphtha to the steam cracker; and passing the light naphtha to the paraffin separation system.

* * * * *